US005885794A

United States Patent [19]
Mathews et al.

[11] Patent Number: 5,885,794
[45] Date of Patent: Mar. 23, 1999

[54] RECOMBINANT PRODUCTION OF VERTEBRATE ACTIVIN RECEPTOR POLYPEPTIDES AND IDENTIFICATION OF RECEPTOR DNAS IN THE ACTIVIN/TGF-β SUPERFAMILY

[75] Inventors: Lawrence S. Mathews, San Diego; Wylie W. Vale, La Jolla, both of Calif.

[73] Assignee: The Salk Institute for Biological Studies, La Jolla, Calif.

[21] Appl. No.: 300,584

[22] Filed: Sep. 2, 1994

Related U.S. Application Data

[63] Continuation of Ser. No. 880,220, May 8, 1992, abandoned, which is a continuation-in-part of Ser. No. 773,229, Oct. 9, 1991, abandoned, which is a continuation-in-part of Ser. No. 698,709, May 10, 1991, abandoned.

[51] Int. Cl.$^6$ .......................... C12N 15/12; C07K 14/71; C12Q 1/68
[52] U.S. Cl. .................. 435/69.1; 536/23.5; 536/24.31; 435/320.1; 435/325; 435/252.3; 435/254.11; 435/6
[58] Field of Search ............................. 435/69.1, 240.2, 435/252.3, 172.3, 325, 254.11, 6, 91.2, 320.1; 530/350; 536/23.5, 24.31

[56] References Cited

U.S. PATENT DOCUMENTS

| | | | |
|---|---|---|---|
| 4,973,577 | 11/1990 | Vale, Jr. et al. | 514/12 |
| 5,216,126 | 6/1993 | Cox | 530/350 |

OTHER PUBLICATIONS

Shimasaki, S. *PNAS* 85: 4218–4222 (1988).
Ignotz and Massague, "Cell Adhesion Protein Receptors as Targets for Transforming Growth Factor–β Action", Cell vol. 51:189–197 (1987).
Nakamura et al., "Activin–Binding Protein from Rat Ovary Is Follistatin", Science vol. 247:836–838 (1990).
Lim et al., "Regulation of Growth Hormone (GH) Bioactivity by a Recombinant Human GH–Binding Protein", Endocrinology vol. 127:1287–1291 (1990).
Massague et al., "TGF–β Receptors and TGF–β Binding Proteoglycans: Recent Progress in Identifying Their Functional Properties", Annals of the New York Academy of Sciences vol. 593:59–72 (1990).
Laiho et al., "Concomitant Loss of Transforming Growth Factor (TGF)–β Receptor Types I and II TGF–β–resistant Cell Mutants Implicates Both Receptor Types in Signal Transduction", Journal of Biological Chemistry, vol. 265:18518–18524 (1990).
Vale et al., "The Inhibin/Activin Family of Hormones and Growth Factors", *Peptide Growth Factors and Their Receptors II*, Chapter 26; pp. 211–248 (Springer–Verlag Berlin 1990).

Mathews and Vale, "Expression Cloning of an Activin Receptor, a Predicted Transmembrane Serine Kinase," Cell, vol. 65:973–982 (1991).
Hanks et al., "The Protein Kinase Family: Conserved Features and Deduced Phylogeny of the Catalytic Domains," Science vol. 241:42–52 (1988).
Kondo et al., "Activin Receptor mRNA Is Expressed Early In Xenopus Embryogenesis And The Level Of The Expression Affects The Body Axis Formation", Biochemical and Biophysical Research Communications vol. 181:684–690 (1991).
Attisano et al., "Novel Activin Receptors: Distinct Genes and Alternative mRNA Splicing Generate a Repertoire of Serine/Threonine Kinase Receptors", Cell vol. 68:97–108 (1992).
Lin et al., "Expression Cloning of the TGF–β Type II Receptor, a Functional Transmembrane Serine/Threonine Kinase", Cell vol. 68:775–785 (1992).
Mathews et al., "Cloning of a Second Type of Activin Receptor and Functional Characterization in Xenopus Embryos", Science vol. 255:1702–1705 (1992).
Donaldson et al., "Molecular Cloning and Binding Properties of the Human Type II Activin Receptor", Biochemical and Biophysical Research Communications vol. _:_–_ (Apr. 15, 1992).

*Primary Examiner*—David L. Fitzgerald
*Attorney, Agent, or Firm*—Stephen E. Reiter; Gray Cary Ware & Freidenrich LLP

[57] ABSTRACT

In accordance with the present invention, there are provided novel receptor proteins characterized by having the following domains, reading from the N-terminal end of said protein:

an extracellular, ligand-binding domain, a hydrophobic, trans-membrane domain, and an intracellular, receptor domain having serine kinase-like activity.

The invention receptors optionally further comprise a second hydrophobic domain at the amino terminus thereof. The invention receptor proteins are further characterized by having sufficient binding affinity for at least one member of the activin/TGF-β superfamily of polypeptide growth factors such that concentrations of $\leq 10$ nM of said polypeptide growth factor occupy $\geq 50\%$ of the binding sites of said receptor protein. A presently preferred member of the invention superfamily of receptors binds specifically to activins, in preference to inhibins, transforming growth factor-β, and other non-activin-like proteins. DNA sequences encoding such receptors, assays employing same, as well as antibodies derived therefrom, are also disclosed.

32 Claims, 6 Drawing Sheets

Divide a cDNA library in a mammalian expression vector into pools of 1000 clones, prepare DNA from each pool Transfect COS cells directly on microscope slides Bind [125I] activin A, wash cells, fix, dip in photographic emulsion Subdivide bacteria from positive pool and rescreen; repeat until receptor clone is pure

```
Act R  (174) L LLEVKGREGFV VWKAQLENVAVKIF FP DDKQSWQEEVYSLPGMHHNL QEIGAEKRCT SVDVLWL ITA
Daf    (295) L LTGRVGRFGFV VNSRGDYIEVAVKIF FNAD DEPAFHEEE IFETRMLHHNL RIGSDRVLTGFVTELWLVLE
Subdomain         I                    II                III                 IV Act R   HFHGSLSDFLNAV VSWNELCHIAETAIGLAAHHEI IGKIDGKPAAIRDIKSN VLNN LT AC( ) EL
Daf     HYHGSLSDFLNEV TVNIETYNLMRGAIGLAAHHNI IGKIKESKPAAMIRDIKSN IMNITC () IL
Subdomain   V                       VIA                              VIB               VII Act R   LALKF.. AEAGKSAGDTHGGT RYIAPELLEGAIFQR.DAFLRDDYAMIVWELARCTADG IV DEYMLP
Daf     LSLSKPEAAASDIIANENYGLGT RYIAPEHLNSTMEFTVFESYQCDDYSFIVWETLQRC..EDGIVLPREAA
Subdomain             VIII                                      IX Act R   FE..E.EEIGEIPSLEMQVV VVHKIRE PVLRDWQEHAMAMLEIIECWDHDAFARLSAGCVGERITQMQRL  (28)
Daf     TVIPEIEWTDEPPQDMMEVVVCTRFRE PTENHWKEHPMKHIEILKCWNGNPAR FTSYICRFMDERQQL  (78)
Subdomain      X                                       XI
```

FIG. 4

RECOMBINANT PRODUCTION OF VERTEBRATE ACTIVIN RECEPTOR POLYPEPTIDES AND IDENTIFICATION OF RECEPTOR DNAS IN THE ACTIVIN/TGF-β SUPERFAMILY

RELATED APPLICATION

This application is a continuation of application Ser No. 07/880,220 filed May 8, 1992, now abandoned which is a continuation-in-part of U.S. Ser. No. 773,229, filed Oct. 9, 1991, now abandoned which is, in turn, a continuation-in-part of U.S. Ser. No. 698,709, filed May 10, 1991, now abandoned.

ACKNOWLEDGEMENT

This invention was made with Government support under Grant Numbers HD 13527 and DK 26741, awarded by the National Institutes of Health. The Government has certain rights in this invention.

FIELD OF THE INVENTION

The present invention relates to receptor proteins, DNA sequences encoding same, and various uses therefor.

BACKGROUND OF THE INVENTION

Activins are dimeric proteins which have the ability to stimulate the production of follicle stimulating hormone (FSH) by the pituitary gland. Activins share a common subunit with inhibins, which inhibit FSH secretion.

Activins are members of a superfamily of polypeptide growth factors which includes the inhibins, the transforming growth factors-β (TGF-β), Mullerian duct inhibiting substance, the Drosophila decapentaplegic peptide, several bone morphogenetic proteins, and the Vg-related peptides.

As a result of their extensive anatomical distribution and multiple biological actions, members of this superfamily of polypeptide growth factors are believed to be involved in the regulation of numerous biological processes. Activin, for example, is involved in the proliferation of many tumor cell lines, the control of secretion and expression of the anterior pituitary hormones (e.g., FSH, GH and ACTH), neuron survival, hypothalamic oxytocin secretion, erythropoiesis, placental and gonadal steroidogenesis, early embryonic development, and the like.

Other members of the activin/TGF-β superfamily of polypeptide growth factors are involved in the regulation of cell function and cell proliferation for numerous cell types, in adults and embryos. For example, cells which are subject to regulation by one or more members of the activin/TGF-β superfamily of polypeptide growth factors include mesenchymal cells, muscle cells, skeletal cells, immune cells, hematopoietic cells, steroidogenic cells, endothelial cells, liver cells, epithelial cells, and the like.

Chemical cross-linking studies with a number of cell types suggests that multiple binding sites (i.e., receptors) exist on the surface of cells. However, little is known about the structure of these receptors, or about the second messenger signalling systems that they employ. It would be desirable, therefore, if the nature of these poorly characterized receptor proteins could be more fully understood.

BRIEF DESCRIPTION OF THE INVENTION

In accordance with the present invention, we have identified and characterized members of a new superfamily of receptor proteins which comprise three distinct domains: an extracellular, ligand-binding domain, a hydrophobic, transmembrane domain, and an intracellular, receptor domain having serine kinase-like activity.

Also provided are DNAs encoding the above-described receptor proteins, and antibodies thereto, as well as bioassays, therapeutic compositions containing such proteins and/or antibodies, and applications thereof.

The DNAs of the invention are useful as probes for the identification of additional members of the invention superfamily of receptor proteins, and as coding sequences which can be used for the recombinant expression of the invention receptor proteins, or functional fragments thereof. The invention receptor proteins, and antibodies thereto, are useful for the diagnosis and therapeutic management of carcinogenesis, wound healing, disorders of the immune, reproductive, or central nervous systems, and the like.

BRIEF DESCRIPTION OF THE FIGURES

FIG. 4 presents a comparison between activin receptor and daf-1 [a C. elegans gene encoding a putative receptor protein kinase (with unknown ligand); see Georgi, et al., Cell 61: 635–645 (1990)]. Conserved residues between the activin receptor and daf-1 are highlighted; conserved kinase domain residues are designated with an "*".

DETAILED DESCRIPTION OF THE INVENTION

In accordance with the present invention, there is provided a novel superfamily of receptor protein(s) characterized by having the following domains, reading from the N-terminal end of said protein:

an extracellular, ligand-binding domain, a hydrophobic, trans-membrane domain, and an intracellular domain having serine kinase-like activity.

The novel receptor protein(s) of the invention optionally further comprise a second hydrophobic domain at the amino terminus thereof.

Figure 1:
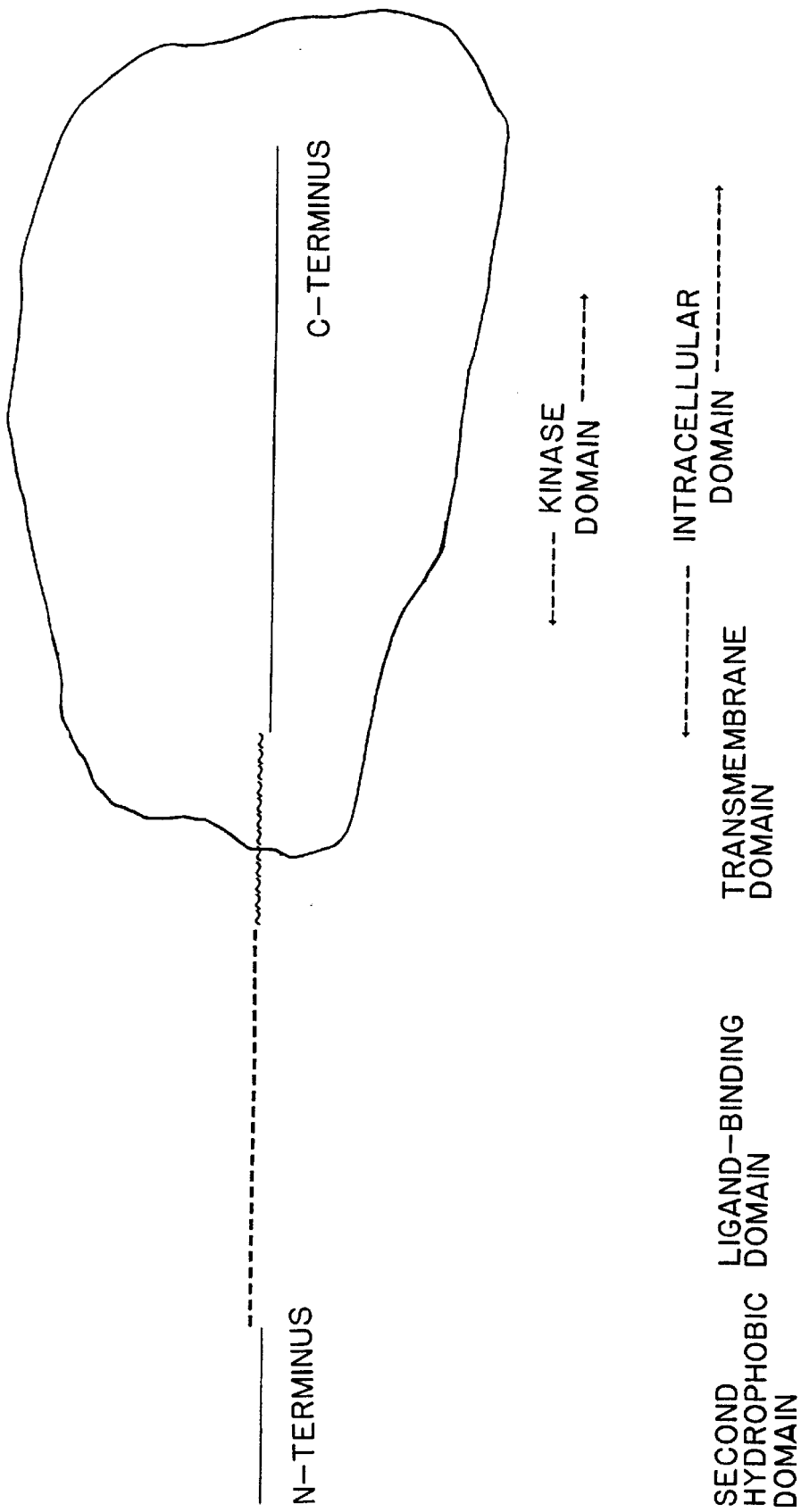
FIG. 1 is a schematic diagram of receptors of the invention and the various domains thereof.
Figure 2:
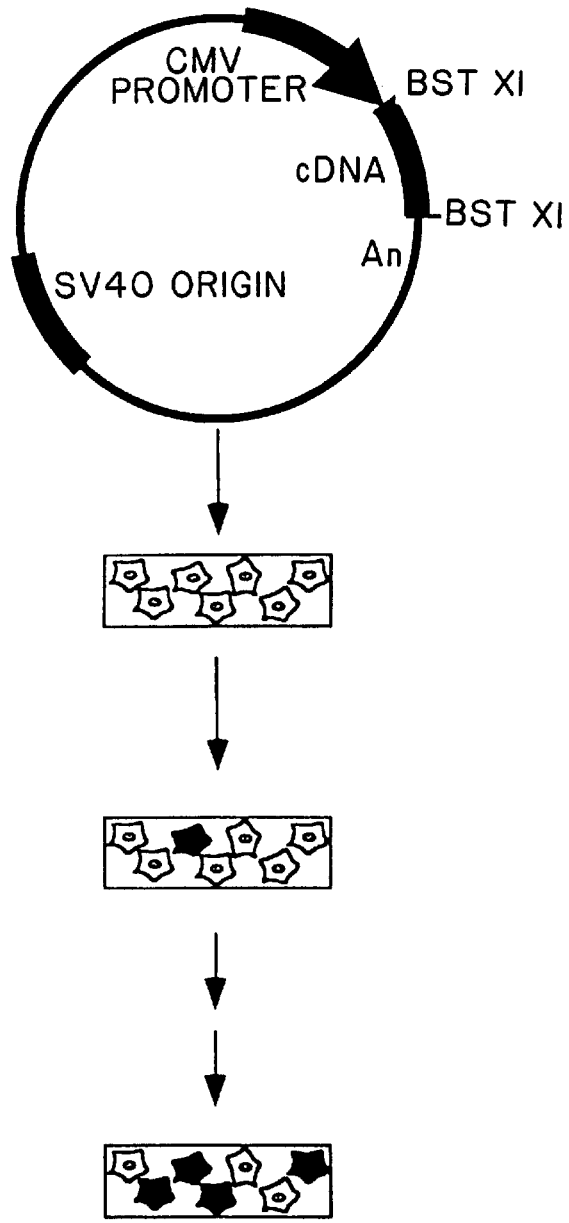
FIG. 2 outlines the strategy used for expression cloning of a receptor of the activin/TGF-β receptor superfamily.

As employed herein, the phrase "extracellular, ligand-binding domain" refers to that portion of receptors of the invention which has a high affinity for ligand, and which, when associated with a cell, resides primarily outside of the cell membrane. Because of its location, this domain is not exposed to the processing machinery present within the cell, but is exposed to all components of the extracellular medium. See FIG. 1.

As employed herein, the phrase "hydrophobic, trans-membrane domain" refers to that portion of receptors of the invention which traverses the cell membrane, and serves as a "bridge" between the extracellular and intracellular domains of the receptor. The hydrophobic nature of this domain serves to anchor the receptor to the cell membrane. See FIG. 1.

As employed herein, the phrase "intracellular domain having serine kinase-like activity" refers to that portion of receptors of the invention which resides within the cytoplasm, and which embodies the catalytic functionality characteristic of all receptors of the invention. See FIG. 1.

The optional second hydrophobic domain, positioned at the amino terminus of receptors of the invention, comprises a secretion signal sequence which promotes the intracellular transport of the initially expressed receptor protein across the Golgi membrane. See FIG. 1.

Members of the invention superfamily of receptors can be further characterized as having sufficient binding affinity for at least one member of the activin/TGF-β superfamily of polypeptide growth factors such that concentrations of ≦10 nM of said polypeptide growth factor occupy ≧50% of the binding sites of said receptor protein.

Binding affinity (which can be expressed in terms of association constants, Ka, or dissociation constants, Kd) refers to the strength of interaction between ligand and receptor, and can be expressed in terms of the concentration of ligand necessary to occupy one-half (50%) of the binding sites of the receptor. A receptor having a high binding affinity for a given ligand will require the presence of very little ligand to become at least 50% bound (hence the Kd value will be a small number); conversely, receptor having a low binding affinity for a given ligand will require the presence of high levels of ligand to become 50% bound (hence the Kd value will be a large number).

Reference to receptor protein "having sufficient binding affinity such that concentrations of said polypeptide growth factor less than or equal to 10 nM (i.e., ≦10 nM) occupy ≧50% (i.e., greater than or equal to one-half) of the binding sites of said receptor protein" means that ligand (i.e., polypeptide growth factor) concentration(s) of no greater than about 10 nM are required in order for the ligand to occupy at least 50% of the active sites of said receptor, with much lower ligand concentrations typically being required. Presently preferred receptors of the present invention have a binding affinity such that ligand concentration(s) in the range of only about 100–500 pM are required in order to occupy (or bind to) at least 50% of the receptor binding sites.

Members of the invention superfamily of receptors can be divided into various subclasses, based on the approximate size of the crosslinked complexes obtained when radiolabeled activin is chemically crosslinked to cell extracts [see, for example, Example VI below, or Mathews and Vale in Cell 65: 973–982 (1991)]. Type I activin/TGF-β receptors are those which form a crosslinked complex of about 65 kD with activin; Type II receptors are those which form a crosslinked complex of about 80–85 kD with activin; while Type III, Type IV and the like receptors are those which form crosslinked complexes with activin having molecular weights greater than about 100 kD.

Each member of a given subclass is related to other members of the same subclass by the high degree of homology (e.g., >80% overall amino acid homology; frequently having >90% overall amino acid homology) between such receptors; whereas members of a given subclass differ from members of a different subclass by the lower degree of homology (e.g., at least about 30% up to 80% overall amino acid homology; with in the range of about 40% up to 90% amino acid homology specifically in the kinase domains thereof) between such receptors. Typically, related receptors have at least 50% overall amino acid homology; with at least about 60% amino acid homology in the kinase domains thereof. Preferably, related receptors are defined as those which have at least 60% overall amino acid homology; with at least about 70% amino acid homology in the kinase domains thereof.

Based on the above criteria, the receptors described herein are designated Type II receptors, with the first discovered Type II receptor (i.e., the mouse-derived activin receptor) being designated ActRII, while subsequently identified Type II receptors which are not homologs of ActRII (because while clearly related by size and some sequence homology, they differ sufficiently to be considered as variants of ActRII), are designated ActRIIB, ActRIIC, etc.

Presently preferred members of the invention superfamily of receptors are further characterized by having a greater binding affinity for activins than for inhibins. Such receptors are frequently also observed to have:

substantially no binding affinity for transforming growth factors-β, and substantially no binding affinity for non-activin-like proteins or compounds.

Additional members of the invention superfamily of receptors are further characterized by having a greater binding affinity for inhibins than for activins or TGF-βs.

Additional members of the invention superfamily of receptors are further characterized by having a greater binding affinity for TGF-βs than for activins or inhibins.

As employed herein, "activin" refers to activin A (a homodimer of two inhibin $β_A$ subunits), activin B (a homodimer of two inhibin $β_B$ subunits), activin AB (a heterodimer composed of one inhibin $β_A$ subunit and one inhibin $β_B$ subunit); "inhibin" refers to inhibin A (composed of the inhibin α subunit and an inhibin $β_A$ subunit), inhibin B (composed of the inhibin α subunit and an inhibin $β_B$ subunit); "transforming growth factor β or TGF-β" refers to TGF-β1 (a homodimer of two TGF-β1 subunits), TGF-β2 (a homodimer of two TGF-β2 subunits), TGF-β3 (a homodimer of two TGF-β3 subunits), TGF-β4 (a homodimer of two TGF-β4 subunits), TGF-β5 (a homodimer of two TGF-β5 subunits), TGF-β1.2 (a heterodimer of one TGF-β1 subunit and one TGF-β2 subunit), and the like.

Transforming growth factors-β (TGF-βs) are members of the activin/TGF-β superfamily of polypeptide growth factors. TGF-βs are structurally related to activins, sharing at least 20–30% amino acid sequence homology therewith. TGF-βs and activins have a substantially similar distribution pattern of cysteine residues (or substitution) throughout the peptide chain. Furthermore, both polypeptides, in their active forms, are dimeric species.

As employed herein, the term "non-activin-like" proteins refers to any protein having essentially no structural similarity with activins (as defined broadly herein).

Preferred members of the invention superfamily of receptors comprise those having in the range of about 500 amino acids, and are further characterized by having the following designated sizes for each of the domains thereof, reading from the N-terminal end of said receptor:

the extracellular, ligand-binding domain preferably will have in the range of about 114–118 amino acids, the hydrophobic, trans-membrane domain preferably will have in the range of about 23–28 amino acids, beginning at the carboxy terminus of the extracellular domain, and the intracellular domain having kinase-like activity preferably will have in the range of about 345–360 amino acids, beginning at the carboxy terminus of the hydrophobic, trans-membrane domain.

Receptors of the invention optionally further comprise a second hydrophobic domain having in the range of about 16–30 amino acids at the extreme amino terminus thereof (i.e., at the amino terminus of the extracellular, ligand-binding domain). This domain is a secretion signal sequence, which aids the transport of invention receptor(s) across the cell membrane. Exemplary secretion signal sequences include amino acids 1–19 of Sequence ID No. 1, amino acids 1–20 of Sequence ID No. 3, and the like. Such secretion signal sequences can be encoded by such nucleic acid sequences as nucleotides 71–127 of Sequence ID No. 1, nucleotides 468–527 of Sequence ID No. 3, and the like.

Members of the invention superfamily of receptors can be obtained from a variety of sources, such as, for example, pituitary cells, placental cells, hematopoietic cells, brain cells, gonadal cells, liver cells, bone cells, muscle cells, endothelial cells, epithelial cells, mesenchymal cells, kidney cells, and the like. Such cells can be derived from a variety of organisms, such as, for example, human, mouse, rat, ovine, bovine, porcine, frog, chicken, fish, mink, and the like.

Presently preferred amino acid sequences encoding receptor proteins of the invention include the sequence set forth in Sequence ID No. 2 (which represents a mouse activin receptor amino acid sequence), a modified form of Sequence ID No. 2 wherein the arginine at residue number 39 is replaced by a lysine, the isoleucine at residue number 92 is replaced by a valine, and the glutamic acid at residue number 288 is replaced by a glutamine (which modified form of Sequence ID No. 1 is referred to hereinafter as "Sequence ID No. 1'", and represents a human activin receptor amino acid sequence), and the sequence set forth as Sequence ID No. 4 (which represents a Xenopus activin receptor amino acid sequence), as well as functional, modified forms thereof. Those of skill in the art recognize that numerous residues of the above-described sequences can be substituted with other, chemically, sterically and/or electronically similar residues without substantially altering the biological activity of the resulting receptor species.

In accordance with another embodiment of the present invention, there is provided a soluble, extracellular, ligand-binding protein, further characterized by:

having sufficient binding affinity for at least one member of the activin/TGF-β superfamily of polypeptide growth factors such that concentrations of $\leq 10$ nM of said polypeptide growth factor occupy $\geq 50\%$ of the binding sites on said receptor protein, and having at least about 30% sequence identity with respect to:

the sequence of amino acids 20–134 set forth in Sequence ID No. 2;

the sequence of amino acids 20–134 set forth in Sequence ID No. 2, wherein the arginine residue at position number 39 is replaced by a lysine, and the isoleucine at residue number 92 is replaced by a valine; or the sequence of amino acids 21–132 set forth in Sequence ID No. 4.

Presently preferred soluble, extracellular, ligand-binding proteins contemplated by the present invention can be further characterized by having at least about 50% sequence identity with respect to:

the sequence of amino acids 20–134 set forth in Sequence ID No. 2;

the sequence of amino acids 20–134 set forth in Sequence ID No. 2, wherein the arginine residue at position number 39 is replaced by a lysine, and the isoleucine at residue number 92 is replaced by a valine; or the sequence of amino acids 21–132 set forth in Sequence ID No. 4;

with the presently most preferred soluble, extracellular, ligand-binding proteins having at least about 80% sequence identity with respect to the above-referenced fragments of Sequence ID Nos. 2 or 4.

Members of the class of soluble, ligand-binding proteins contemplated by the present invention may be divided into various subclasses, as previously described, wherein members of one subclass may have a greater binding affinity for activins than for inhibins and/or TGF-βs; or alternatively, members of another subclass may have a greater binding affinity for inhibins than for activins and/or TGF-βs; or alternatively, members of yet another subclass may have a greater binding affinity for TGF-βs than for activins and/or inhibins. It is, of course, understood by those of skill in the art, that members of more than one subclass may have a greater binding affinity for one member of the activin/TGF-β superfamily of polypeptide growth factors, relative to other members of the superfamily.

Presently preferred soluble, extracellular, ligand-binding proteins of the present invention are further characterized by:

having a greater binding affinity for activins than for inhibins, having substantially no binding affinity for transforming growth factors-β, and having substantially no binding affinity for non-activin-like proteins.

Presently preferred soluble, extracellular, ligand-binding proteins of the present invention typically comprise in the range of about 114–118 amino acids.

Especially preferred soluble, extracellular, ligand-binding proteins of the invention are those having substantially the same amino acid sequence as that set forth as:

residues 20–134 of Sequence ID No. 2;
residues 20–134 of Sequence ID No. 2, wherein the arginine residue at position number 39 is replaced by a lysine, and the isoleucine at residue number 92 is replaced by a valine; or
residues 21–132 of Sequence ID No. 4.

As employed herein, the term "substantially the same amino acid sequence" refers to amino acid sequences having at least about 80% identity with respect to the reference amino acid sequence, and will retain comparable functional and biological properties characteristic of the protein encoded by the reference amino acid. Preferably, proteins having "substantially the same amino acid sequence" will have at least about 90% amino acid identity with respect to the reference amino acid sequence; with greater than about 95% amino acid sequence identity being especially preferred.

The above-described soluble proteins can be employed for a variety of therapeutic uses, e.g., to block receptors of the invention from affecting processes which the receptors would otherwise mediate. The presence of the soluble proteins of the invention will compete with functional ligand for the receptor, preventing the formation of a functional receptor-ligand complex, thereby blocking the normal regulatory action of the complex.

In accordance with yet another embodiment of the present invention, there are provided antibodies generated against the above-described soluble proteins and receptor proteins. Such antibodies can be employed for diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins as antigens for antibody production.

In accordance with still another embodiment of the present invention, there are provided methods for modulating the transcription trans-activation of receptor(s) of the invention by contacting said receptor(s) with a modulating, effective amount of the above-described antibodies.

The soluble proteins of the invention, and the antibodies of the invention, can be administered to a subject employing standard methods, such as, for example, by intraperitoneal, intramuscular, intravenous, or subcutaneous injection, implant or transdermal modes of administration, and the like. In addition, methods such as transfection with viral or retroviral vectors encoding the invention compositions. One of skill in the art can readily determine dose forms, treatment regiments, etc, depending on the mode of administration employed.

In accordance with a further embodiment of the present invention, there are provided DNA sequences which encode the above-described soluble proteins and receptor proteins. Optionally, such DNA sequences, or fragments thereof, can be labeled with a readily detectable substituent (to be used, for example, as a hybridization probe).

The above-described receptor(s) can be encoded by numerous DNA sequences, e.g., a DNA sequence having a contiguous nucleotide sequence substantially the same as:

nucleotides 128–1609 of Sequence ID No. 1 (which encodes a mouse activin receptor);
variations of nucleotides 128–1609 of Sequence ID No. 1, wherein the codon for residue number 39 of the encoded amino acid codes for lysine, the codon for residue number 92 of the encoded amino acid codes for valine, and the codon for residue number 288 of the encoded amino acid encodes glutamine (which encodes a human activin receptor);
nucleotides 528–1997 of Sequence ID No. 3 (which encodes a Xenopus activin receptor); or
variations of any of the above sequences which encode the same amino acid sequences, but employ different codons for some of the amino acids.

As employed herein, the term "substantially the same as" refers to DNA having at least about 70% homology with respect to the nucleotide sequence of the DNA fragment with which subject DNA is being compared. Preferably, DNA "substantially the same as" a comparative DNA will be at least about 80% homologous to the comparative nucleotide sequence; with greater than about 90% homology being especially preferred.

Another DNA which encodes a receptor of the invention is one having a contiguous nucleotide sequence substantially the same as:

nucleotides 71–1609 of Sequence ID No. 1 (which encodes a precursor-form of a mouse activin receptor);
variations of nucleotides 71–1609 of Sequence ID No. 1, wherein the codon for residue number 39 of the encoded amino acid codes for lysine, the codon for residue number 92 of the encoded amino acid codes for valine, and the codon for residue number 288 of the encoded amino acid encodes glutamine (which encodes a precursor-form of a human activin receptor);
nucleotides 468–1997 of Sequence ID No. 3 (which encodes a precursor form of a Xenopus activin receptor); or
variations of any of the above sequences which encode the same amino acid sequences, but employ different codons for some of the amino acids.

Yet another DNA which encodes the above-described receptor is one having a contiguous nucleotide sequence substantially the same as set forth in Sequence ID No. 1, Sequence ID No. 1' or Sequence ID No. 3.

In accordance with a further embodiment of the present invention, the receptor-encoding cDNAs can be employed to probe library(ies) (e.g., cDNA, genomic, and the like) for additional sequences encoding novel receptors of the activin/TGF-β superfamily. In accordance with a particular embodiment of the present invention, there is provided an isolated probe having the nucleotide sequence of a fragment of the coding or noncoding strand of the receptor cDNA molecule, wherein the probe specifically hybridizes to the receptor cDNA in a vertebrate library under low stringency hybridization conditions. Such screening is initially carried out under low-stringency conditions, which comprise a temperature of less than about 42° C., a formamide concentration of less than about 50%, and a moderate to low salt concentration. Presently preferred conditions for such screening comprise a temperature of about 37° C., a formamide concentration of about 20%, and a salt concentration of about 5×standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology for the identification of a stable hybrid. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe.

In accordance with yet another embodiment of the present invention, there is provided a method for the recombinant production of receptor(s) of the invention by expressing the above-described DNA sequences in suitable host cells.

The use of a wide variety of recombinant organisms has been described for the production of peptides. One of skill in the art can readily determine suitable hosts (and expression conditions) for use in the recombinant production of the peptides of the present invention. Yeast hosts, bacterial hosts, mammalian hosts, and the like can be employed. Regulatory sequences capable of controlling the expression of invention peptides are well known for each of these host systems, as are growth conditions under which expression occurs.

In accordance with a further embodiment of the present invention, there is provided a binding assay employing receptors of the invention, whereby a large number of compounds can be rapidly screened to determine which compounds, if any, are capable of binding to the receptors of the invention. Then, more detailed assays can be carried out with those compounds found to bind, to further determine whether such compounds act as agonists or antagonists of invention receptors.

Another application of the binding assay of the invention is the assay of test samples (e.g., biological fluids) for the presence or absence of members of the activin/TGF-β superfamily of polypeptide growth factors. Thus, for example, serum from a patient displaying symptoms related to pathway(s) mediated by members of the activin/TGF-β superfamily of polypeptide growth factors can be assayed to determine if the observed symptoms are perhaps caused by over- or under-production of such polypeptide growth factor.

The binding assays contemplated by the present invention can be carried out in a variety of ways, as can readily be identified by one of skill in the art. For example, competitive binding assays can be employed, as well as radioimmunoassays, ELISA, ERMA, and the like.

In accordance with a still further embodiment of the present invention, there are provided bioassays for evaluating whether test compounds are capable of acting as agonists or antagonists of receptor(s) of the present invention.

The bioassays of the present invention involve evaluating whether test compounds are capable of acting as either agonists or antagonists for members of the invention superfamily of receptors, or functional modified forms of said receptor protein(s). The bioassay for evaluating whether test compounds are capable of acting as agonists comprises:
  (a) culturing cells containing:
    DNA which expresses said receptor protein(s) or functional modified forms of said receptor protein(s), and
    DNA encoding a hormone response element operatively linked to a reporter gene;
  wherein said culturing is carried out in the presence of at least one compound whose ability to induce transcription activation activity of receptor protein is sought to be determined, and thereafter
  (b) monitoring said cells for expression of the product of said reporter gene.

The bioassay for evaluating whether test compounds are capable of acting as antagonists for receptor(s) of the invention, or functional modified forms of said receptor(s), comprises:
  (a) culturing cells containing:
    DNA which expresses said receptor protein(s), or functional modified forms of said receptor protein(s), and
    DNA encoding a hormone response element operatively linked to a reporter gene wherein said culturing is carried out in the presence of:
      increasing concentrations of at least one compound whose ability to inhibit transcription activation of said receptor protein(s) is sought to be determined, and
      a fixed concentration of at least one agonist for said receptor protein(s), or functional modified forms of said receptor protein(s); and thereafter
  (b) monitoring in said cells the level of expression of the product of said reporter gene as a function of the concentration of said compound, thereby indicating the ability of said compound to inhibit activation of transcription.

Host cells contemplated for use in the bioassay(s) of the present invention, include CV-1 cells, COS cells, and the like; reporter and expression plasmids employed typically also contain the origin of replication of SV-40; and the reporter and expression plasmids employed also typically contain a selectable marker.

The hormone response element employed in the bioassay (s) of the present invention can be selected from, for example, mouse mammary tumor virus long terminal repeat (MTV LTR), mammalian growth hormone promoter, and the reporter gene can be selected from chloramphenicol acetytransferase (CAT), luciferase, β-galactosidase, and the like.

The cells can be monitored for the level of expression of the reporter gene in a variety of ways, such as, for example, by photometric means [e.g., by colorimetry (with a colored reporter product such as β-galactosidase), by fluorescence (with a reporter product such as luciferase), etc], by enzyme activity, and the like.

Compounds contemplated for screening in accordance with the invention bioassays include activin- or TGF-β-like compounds, as well as compounds which bear no particular structural or biological relatedness to activin or TGF-β.

As employed herein, the phrase "activin- or TGF-β-like compounds" includes substances which have a substantial degree of homology (at least 20% homology) with the amino acid sequences of naturally occurring mammalian inhibin alpha and $\beta_A$ or $\beta_B$ chains (either singly or in any combination) as well as alleles, fragments, homologs or derivatives thereof which have substantially the same qualitative biological activity as mammalian inhibin, activin, or TGF-β. Examples of activin- or TGF-β-like compounds include activin A (a homodimer of two inhibin $\beta_A$ subunits), activin B (a homodimer of two inhibin $\beta_B$ subunits), activin AB (a heterodimer composed of one inhibin $\beta_A$ subunit and one inhibin $\beta_B$ subunit), inhibin A (composed of the inhibin α subunit and an inhibin $\beta_A$ subunit), inhibin B (composed of the inhibin α subunit and an inhibin $\beta_B$ subunit), TGF-β1 (a homodimer of two TGF-β1 subunits), TGF-β2 (a homodimer of two TGF-β2 subunits), TGF-β3 (a homodimer of two TGF-β3 subunits), TGF-β4 (a homodimer of two TGF-β4 subunits), TGF-β5 (a homodimer of two TGF-β5 subunits), TGF-β1.2 (a heterodimer of one TGF-β1 subunit and one TGF-β2 subunit), and the like.

Examples of compounds which bear no particular structural or biological relatedness to activin or TGF-β, but which are contemplated for screening in accordance with the bioassays of the present invention, include any compound that is capable of either blocking the action of the invention receptor peptides, or promoting the action of the invention receptor peptides, such as, for example, alkaloids and other heterocyclic organic compounds, and the like.

The method employed for cloning the receptor(s) of the present invention involves expressing, in mammalian cells, a cDNA library of any cell type thought to respond to members of the activin/TGF-β superfamily of polypeptide growth factors (e.g., pituitary cells, placental cells, fibroblast cells, and the like). Then, the ability of the resulting mammalian cells to bind a labeled receptor ligand (i.e., a labeled member of the activin/TGF-β superfamily of polypeptide growth factors) is determined. Finally, the desired cDNA insert(s) are recovered, based on the ability of that cDNA, when expressed in mammalian cells, to induce (or enhance) the binding of labeled receptor ligand to said cell.

In addition to the above-described applications of the receptor proteins and DNA sequences of the present invention, the receptor or receptor-encoding compositions of the invention can be used in a variety of ways. For example, since activin is involved in many biological processes, the activin receptor (or antibodies thereto) can be applied to the modulation of such biological processes. For example, the stimulation of FSH release by activin can either be enhanced (for example, by supplying the subject with increased amounts of the activin receptor, relative to the amount of endogenous receptor, e.g., by transfecting the subject with a tissue specific activin-encoding construct), or depressed (e.g., by administration to a subject of antibodies to the activin receptor, thereby preventing formation of activin-receptor complex, which would then act to stimulate the release of FSH). Thus, the compositions of the present invention can be applied to the control of fertility in humans, domesticated animals, and animals of commercial interest.

As another example, the effect of activin on mitosis of red and white blood cells can be modulated, for example, by administering to a subject (employing suitable means of administration) a modulating, effective amount of activin receptor (which would enhance the ability of activin present in the cell to modulate mitosis). Alternatively, one could administer to a subject an antibody to the activin receptor (or a portion thereof), which would reduce the effect of activin by blocking the normal interaction between activin and activin receptor.

As additional examples of the wide utility of the invention compositions, receptors and/or antibodies of the invention can be used in such areas as the diagnosis and/or treatment of activin-dependent tumors, enhancing the survival of brain neurons, inducing abortion in livestock and other domesticated animals, inducing twinning in livestock and other domesticated animals, and so on.

As still further examples of the wide utility of the invention compositions, agonists identified for TGF-β specific receptors can be used to stimulate wound healing, to suppress the growth of TGF-β-sensitive tumors, to suppress immune response (and thereby prevent rejection of transplanted organs), and the like. Antagonists or the soluble, ligand-binding domain derived from TGF-β receptors can be used to block endogenous TGF-β, thereby promoting liver regeneration and stimulating some immune responses.

It can be readily seen, therefore, that the invention compositions have utility in a wide variety of diagnostic, clinical, veterinary and research applications.

The invention will now be described in greater detail by reference to the following non-limiting examples.

EXAMPLES

Recombinant human (rh) activin A, rh activin B, and rh inhibin A were generously provided by Genentech, Inc. Porcine TGF-β1 was obtained from R+D Systems.

Double-stranded DNA was sequenced by the dideoxy chain termination method using the Sequenase reagents from US Biochemicals. Comparison of DNA sequences to databases was performed using the FASTA program [Pearson and Lipman, Proc. Natl. Acad. Sci. USA 85: 2444–2448 (1988)].

Example I

Construction and Subdivision of cDNA Library

Polyadenylated RNA was prepared from AtT20 cells using the Fast Track reagents from Invitrogen. cDNA was commercially synthesized and ligated into the plasmid vector pcDNA1 using non-palindromic BstXI linkers, yielding a library of approximately $5 \times 10^6$ primary recombinants. The unamplified cDNA library was plated at 1000 clones per 100 mm plate, then scraped off the plates, frozen in glycerol and stored at −70°.

Activin suppresses adrenocorticotrophic hormone (ACTH) secretion by both primary anterior pituitary cell cultures [Vale et al., Nature 321: 776–779 (1986)] and AtT20 mouse corticotropic cells. Because AtT20 cells possess activin receptors indistinguishable from those on other cell types (based on binding affinity measurements with activin A), these cells were chosen to be the source of cDNA for transfection. A cDNA library of approximately $5 \times 10^6$ independent clones from AtT20 cells was constructed in the mammalian expression vector, pcDNA1, and screened using an expression cloning approach [Gearing et al., EMBO J. 8, 3667–3676 (1989)] based on the ability to detect activin binding to single transfected cells. The library was divided into pools of 1000 clones, DNA was prepared from each pool of clones and transiently transfected into COS cells, and the cells screened for the capacity to bind iodinated activin A. Binding was assessed by performing the transfections and binding reactions directly on chambered microscope slides, then dipping the slides in photographic emulsion and analyzing them under a microscope. Cells which had been transfected with an activin receptor cDNA, and consequently bound radioactive activin, were covered with silver grains. DNA from pools of clones were analyzed either singly or in groups of three. Of 300 pools (approximately 300,000 clones) assayed in this manner, one group of three generated two positive cells when transfected into COS cells. The positive pool (#64) was identified by transfecting and analyzing DNA from each pool of 1000 singly, and then was further fractionated until a single clone (pmActR1) was purified which generated >$10^4$ positive cells after transfection (see Table 1).

TABLE 1

Purification of the activin receptor clone from the AtT20 library

| Pool | Clones/pool | Positive cells/slide |
| --- | --- | --- |
| 62,63,64 | 3x1000 | 2 |
| 64 | 1000 | 1–3 |
| 64–51 | 400 | 4–10 |
| 64–51-R10;64–51-C13 | 20 | 25–40 |
| pmActR1 | 1 | >$10^4$ |

Figure 3:
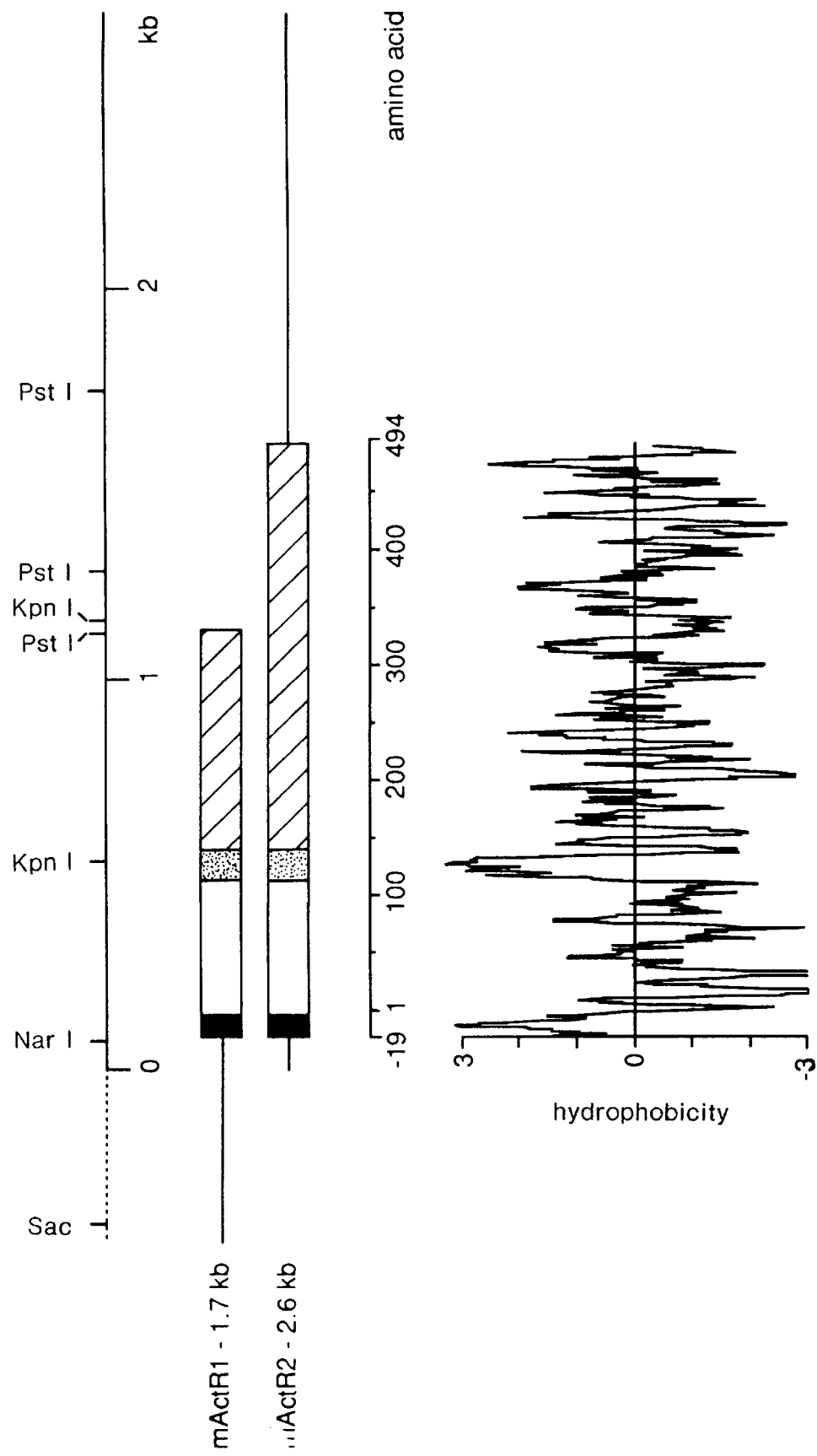
FIG. 3 is a schematic of two mouse activin receptor clones. The top line of the figure is a restriction map, in kb, of mActR1 and mActR2, with numbering starting from bp 1 of mActR2. The dotted line in the figure represents 5' untranslated sequences present only in mActR1. The middle lines present a schematic representation of two activin receptor cDNA clones. Boxes represent coding sequences—black is the signal peptide, white is the extracellular ligand-binding domain, gray is the transmembrane, and the intracellular kinase domain is hatched. Amino acids are numbered beneath the schematics.

The total number of transfected cells capable of binding $^{125}I$ activin A in a field of $2 \times 10^5$ COS cells was counted for pools of clones at each stage of the purification process.

pmActR1 contained a 1.7 kb insert, coding for a protein of 342 amino acids (FIG. 3); however, it was incomplete on the 3' end, thus the last 17 amino acids were encoded by vector sequences. In order to obtain the entire sequence, the AtT20 library was rescreened by hybridization with the 1.6 kb SacI-PstI fragment (FIG. 3). Screening 6×10$^5$ colonies yielded one additional positive clone (pmActR2) which had a 2.6 kb insert and contained the entire coding sequence for the mouse activin receptor (FIG. 3). The nucleic acid sequence and the deduced amino acid sequence of the insert in pmActR2 are set forth in Sequence ID No. 1.

Example II

COS Cell Transfection

Aliquots of the frozen pools of clones were grown overnight in 3 ml cultures of terrific broth, and mini-prep DNA prepared from 1.5 ml using the alkaline lysis method [Maniatis et al. Molecular Cloning (Cold Spring Harbor Laboratory (1982)]. 1/10 of the DNA from a mini-prep (10 Ml of 100 Ml) was used for each transfection.

2×10$^5$ COS cells were plated on chambered microscope slides (1 chamber-Nunc) that had been coated with 20 μg/ml poly-D-lysine and allowed to attach for at least 3 hours. Cells were subjected to DEAE-Dextran mediated transfection as follows. 1.5 ml of serum-free Dulbecco's Modified Eagle's medium (DME) containing 100 mM chloroquine was added to the cells. DNA was precipitated in 200 ml DME/chloroquine containing 500 mg/ml DEAE-Dextran, then added to the cells. The cells were incubated at 37° for 4 hours, then the media was removed and the cells were treated with 10% DMSO in HEPES buffered saline for 2 minutes. Fresh media was added and the cells assayed 3 days later. For transfections with the purified clone, 2.5×10$^6$ cells were transfected in 100 mm dishes with 5 μg purified DNA. The total transfection volume was 10 ml, and the DNA was precipitated in 400 μl.

Example III

Binding Assay

Cells were washed 2× with HEPES buffered saline (HDB) containing 0.1% BSA, then incubated for 90 minutes at 22° in 0.5 ml HDB, 0.1% BSA containing 7×10$^5$ cpm $^{125}$I activin A (approximately 7 ng, 500 pM). The cells were then washed 3× with cold HDB, fixed for 15 minutes at 22° in 2.5% glutaraldehyde/HDB and washed 2× with HDB. The chambers were then peeled off the slides, and the slides dehydrated in 95% ethanol, dried under vacuum, dipped in NTB2 photographic emulsion (Kodak) and exposed in the dark at 4° for 3 days. Following development of the emulsion, the slides were dehydrated in 95% ethanol, stained with eosin and coverslipped with DPX mountian (Electron Microscopy Sciences). The slides were analyzed under darkfield illumination using a Leitz microscope.

Example IV

Subdivision of Positive Pool

Of 300 pools screened (each pool containing about 1000 cDNAs), one positive pool (#64), which produced two positive cells, was identified. Bacteria from the frozen stock of this positive pool (#64) were replated at approximately 400 clones per plate, replica plates were made, and DNA was prepared from each subpool and analyzed employing the binding assay described above. Several positive subpools were found, which generated from 4–10 positive cells per slide. The bacteria from the replica plate of one positive subpool were picked onto a grid, and DNA prepared from pools of clones representing all the rows and all the columns, as described by Wong [Science 228: 810–815 (1985)]. The identification of one positive row and one positive column unambiguously identified a single clone, which when transfected yielded >10$^4$ positive cells/2×10$^5$ cells.

Example V

Radioreceptor Assay

Figure 5A:
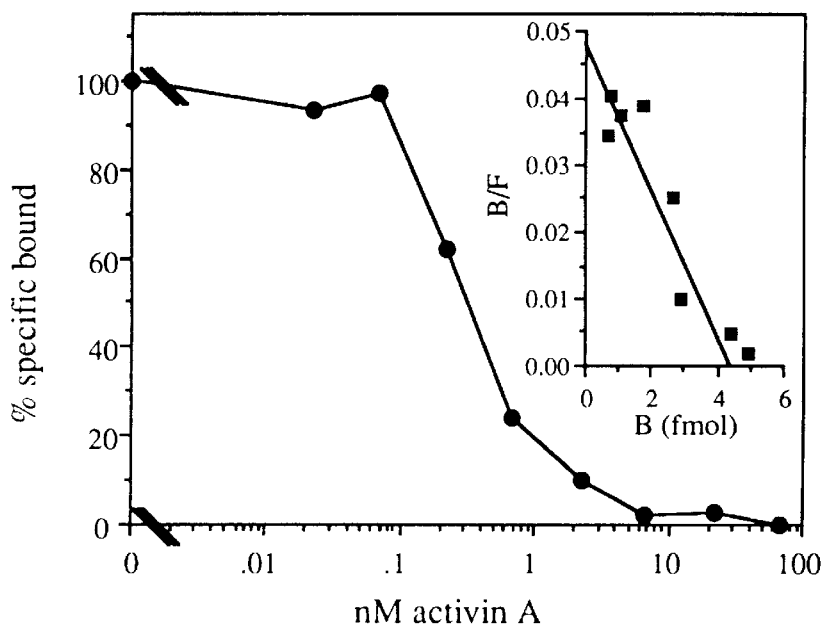
FIG. 5A summarizes results of $^{125}$I activin A binding to COS cells transfected with pmActR1. Binding was competed with unlabeled activin A. For the runs reported herein, total binding was 4.6% of input cpm, non-specific binding was 0.9% of input cpm, and therefore the specific binding was 3.7% of input cpm. Data are shown as % specific binding, normalized to 100%. The inset presents a Scatchard analysis of the data [Ann. NY Acad. Sci. 51: 660–672 (1979)].

10$^5$ COS cells transfected with either pmActR1 or pmActR2, or 10$^6$ untransfected COS cells, were plated in 6 well dishes and allowed to grow overnight. The cells were washed 2× with HDB, 0.1% BSA, and incubated at 22° for 90 minutes in 0.5 ml HDB, 0.1% BSA containing 100,000 cpm (approximately 1 ng, 75 pM) $^{125}$I activin A (5 μg activin A was iodinated by chloramine T oxidation to a specific activity of 50–90 μCi/μg; iodinated activin A was purified on a 0.7×20 cm G-25 column) and varying amounts of unlabeled competitor hormone. Following binding, the cells were washed 3× with cold HDB, solubilized in 0.5 ml 0.5N NaOH, removed from the dish and radioactivity was measured in a gamma counter. Data presented in FIG. 5 are expressed as % specific binding, where 100% specific binding is the difference between binding in the absence of competitor and binding in the presence of a 100 fold molar excess of unlabeled activin A. Binding parameters were determined using the program LIGAND [Munson P. J. and Rodbard, D., Anal. Biochem. 107: 220–259 (1980)].

Example VI

Chemical Cross-linking

2×10$^6$ COS cells, or 5×10$^6$ AtT20 cells, were washed 2× with HDB, scraped off the dish, incubated for 90 minutes at 22° under constant rotation in 0.5 ml HDB containing 7×10$^5$ cpm (approximately 500 pM) $^{125}$I activin A with or without 500 ng (37 nM) unlabeled activin A. Cells were diluted with 1 ml HDB, pelleted by centrifugation and resuspended in 0.5 ml HDB. Disuccinimidyl suberate (DSS; freshly dissolved in DMSO) was added to 500 μM, and the cells incubated at 0° for 30 minutes. The cross-linking was terminated by addition of 1 ml 50 mM Tris-HCl pH 7.5, 100 mM NaCl, then the cells were pelleted by centrifugation, resuspended in 100 μl 50 mM Tris-HCl pH 7.5, 1% Triton X-100 and incubated at 0° for 60 minutes. The samples were centrifuged 5 minutes at 13,000×g, and the Triton-soluble supernatants analyzed by SDS-PAGE using 8.5% polyacrylamide gels. The gels were dried and subjected to autoradiography for 4–14 days.

Example VII

RNA Blot Analysis

Total RNA was purified from tissue culture cells and tissues using LiCl precipitation. 20 μg total RNA was run on 1.2% agarose, 2.2M formaldehyde gels, blotted onto nylon membranes (Hybond-NEN), and hybridized with a 0.6 kb KpnI fragment (see FIG. 3) which had been labeled with $^{32}$p by random priming using reagents from US Biochemicals. Hybridization was performed at 42° in 50% formamide, and the filters were washed at 65° in 0.2×SSC.

Example VIII

Sequence Analysis

Full length mouse activin receptor clone encodes a protein of 513 amino acids, with a 5' untranslated region of 70 bp and a 3' untranslated region of 951 bp. pmActR2 does not contain a poly A tail, although it does have a potential poladenylylation site at bp 2251. The insert in clone pmActR1 had an additional 551 bp of 5' untranslated sequence, was identical in the overlapping range, and stopped at the 3' end at base 1132 of pmActR2. The first methionine codon (ATG), at bp 71, in pmActR2 is in a favorable context for translation initiation [Kozak, M., Nucl. Acids Res. 15: 8125–8148 (1987)], and is preceded by an in-frame stop codon. pmActR1 contains 3 additional ATGs in the 5' untranslated region; however, none of these is in an appropriate context for initiation, and all are followed by in-frame stop codons. While this unusually long 5' leader sequence may have functional significance, it is clearly not necessary for proper expression, because pmActR2, which lacks most of that sequence, can be functionally expressed in COS cells (see below).

Hydropathy analysis using the method of Kyte and Doolittle [J. Mol. Biol. 157: 105–132 (1982)] revealed two hydrophobic regions: a 10 amino acid stretch at the amino terminus assumed to be a single peptide, and a single putative 26 residue membrane-spanning region between amino acids 119–142 (see FIG. 1 and Sequence ID No. 2). The signal peptide contains the conserved n-, h- and c- domains common to signal sequences; the site of cleavage of the signal peptide, before $Ala^1$, is predicted based on rules described by von Heijne [Biochim. Biophys. Act. 947: 307–333 (1988)]. As is common for the cytoplasmic side of membrane-spanning domains, the predicted transmembrane region is closely followed by two basic amino acids. The mature mouse activin receptor is thus predicted to be a 494 amino acid type I membrane protein of Mr 54 kDa, with a 116 amino acid N-terminal extracellular ligand binding domain, and a 346 amino acid intracellular signalling domain.

Comparison of the activin receptor sequence to the sequence databases revealed structural similarity in the intracellular domain to a number of receptor and nonreceptor kinases. Analysis of the sequences of all kinases has led to the identification of a 300 amino acid kinase domain characterized by 12 subdomains containing a number of highly conserved amino acids [Hanks, S. K. and Quinn, A. M., Meth. Enzymol. 200: 38–62 (1991) and Hanks et al., Science 241: 42–52 (1988)]; the activin receptor sequence has all of these conserved subdomains in the proper order (FIG. 4). A conserved Gly in subdomain I is replaced by $Ala^{180}$ in the activin receptor, but this residue has also been observed in other kinases. Based upon structural relatedness, therefore, this receptor is expected to be a functional protein kinase.

The sequences in two of these subdomains (VIB and VIII) can be used to predict tyrosine vs. serine/threonine substrate specificity [Hanks et al., (1988) supra]. The sequence of the mouse activin receptor in both of these subdomains is characteristic of serine kinases.

TABLE 2

| Kinase Domain Predictive Sequences | | | | |
|---|---|---|---|---|
| Subdomain | VIB | SEQ ID NO. | VIII | SEQ ID NO. |
| serine kinase consensus | DLKPEN | 5 | G(T/S)XX(Y/F)X | 6 |
| activin receptor | DIKSKN | 7 | GTRRYM | 8 |
| tyrosine kinase consensus | DLAARN | 9 | XP(I/V) (K/R)W(T/M) | 10 |

Therefore, the activin receptor is expected to have serine/threonine specificity. Furthermore, the activin receptor does not have a tyrosine residue in the standard autophosphorylation region between subdomains VII and VIII, indicating that it is not a standard tyrosine kinase. The receptor could potentially autophosphorylate at $Ser^{333}$ or $Thr^{337}$. One interesting additional possibility is that the activin receptor kinase may have specificity for serine, threonine and tyrosine residues. Several kinases with these properties have recently been described [see, for example, Howell et al., Mol. Cell. Biol. 11: 568–572 (1991), Stern et al., Mol. Cell. Biol. 11: 987–1001 (1991) and Featherstond, C. and Russell, P., Nature 349: 808–811 (1991)].

Figure 6:
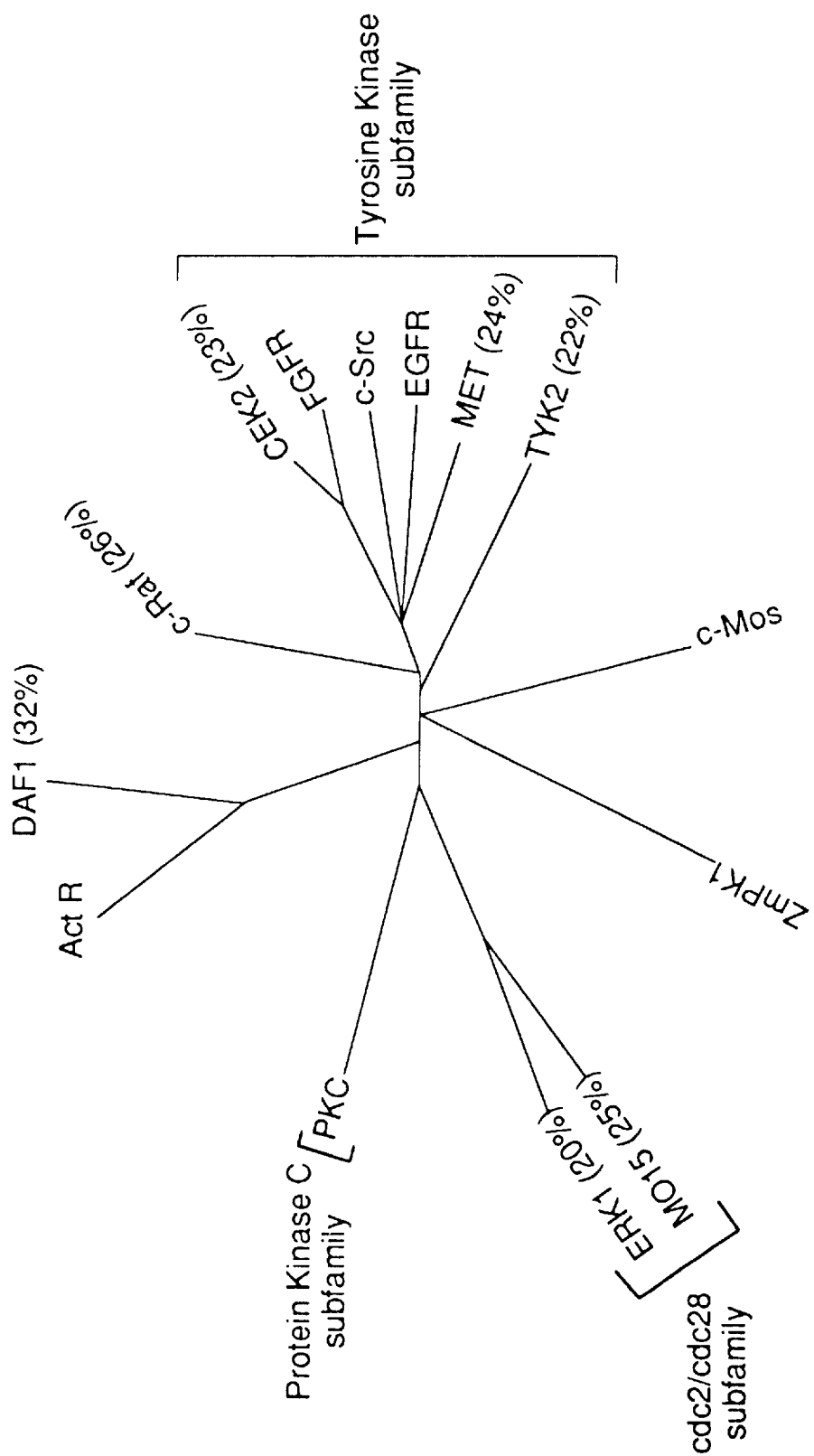
FIG. 6 is a phylogenetic tree, comparing the relationship of the activin receptor kinase domain to other protein kinases. To construct the tree, the catalytic domains of representative sequences were empirically aligned and evolutionary relatedness was calculated using an algorithm designed by Fitch and Margoliash [Science 155: 279–284 (1967)], as implemented by Feng and Doolittle [J. Mol. Evol. 25: 351–360 (1987)]. Known subfamilies of kinases are indicated in the figure. For those sequences that had similarity scores (i.e., a relative sequence identity) of at least 4 standard deviations above the mean (in comparison with all other known kinase sequences), the percent identity with the activin receptor is indicated. For further detail on kinase sequences, the reader is referred to Hanks and Quinn, Meth. Enzymol. 200: 38–62 (1991).

Phylogenetic analysis of the activin receptor compared to 161 other kinase sequences revealed that the activin receptor and the C.elegans protein, daf-1 [Georgi et al., Cell 61: 635–645 (1990)] may constitute a separate subfamily of kinases (see FIG. 6). daf-1 is a putative transmembrane receptor involved in the developmental arrest of a nonfeeding larval state and shares 32% identity with the activin receptor (see FIG. 6). Like the activin receptor, daf-1 is predicted to be a transmembrane serine/threonine-specific kinase; furthermore, both daf and the activin receptor have short, conserved inserts in the kinase domain sequence between subdomains VIA-VIB and X-XI that are not present in any other kinase (underlined in FIG. 4B). This additional similarity lends credence to their belonging to a unique subfamily of kinases. The activin receptor is quite distantly related (18% amino acid sequence identity) to the only other known transmembrane serine/threonine protein kinase, encloded by the ZmPK gene of maize [Walker, J. C. and Zhang, R., Nature 345: 743–746 (1990)].

The extracellular domain of the activin receptor did not show similarity to any other sequences in the databases. This ligand binding domain is relatively small in comparison to those found in other growth factor receptors, but like those receptors this domain has a high cysteine content. The pattern of these Cys residues, however, is not like either an immunoglobulin fold or the cysteine rich repeats of the EGF receptor. There are also two potential sites of N-linked glycosylation in the extracellular domain, as well as a number of potential phosphorylation sites for protein kinase C and casein kinase II in the intracellular domain.

Example IX

Binding Properties of the Cloned Activin Receptor

To verify that the cloned receptor is activin specific, competition binding experiments were performed on COS cells transiently transfected with either pmActR1 or pmActR2. Cells transfected with either construct bound activin A with a single high affinity component (Kd=180 pM; FIG. 5), indicating that a functional (structurally complete) intracellular kinase domain is not required for ligand binding. This binding affinity is consistent with that measured on other activin-responsive cell types [see, for example, Campen, C. A. and Vale, W., Biochem. Biophys. Res. Comm. 157: 844–849 (1988); Hino et al., J. Biol. Chem. 264: 10309–10314 (1989); Sugino et al., J. Biol. Chem. 263: 15249–15252 (1988); and Kondo et al., Biochem. Biophys. Res. Comm, 161: 1267–1272 (1989)]. Untransfected COS cells do not bind activin A. The transfected cultures as a whole expressed approximately 26,000 receptors per cell; however, because only 15% of the cells express the transfected gene (as measured by quantitating transfected cells as a fraction of all cells following dipping in emulsion), each transfected cell expressed an average of 175,000 receptors per cell. The level of expression per cell varies considerably, though, based on the number of accumulated silver grains. This value is comparable to the expression of other transfected cell surface proteins in COS cells.

Figure 5B:
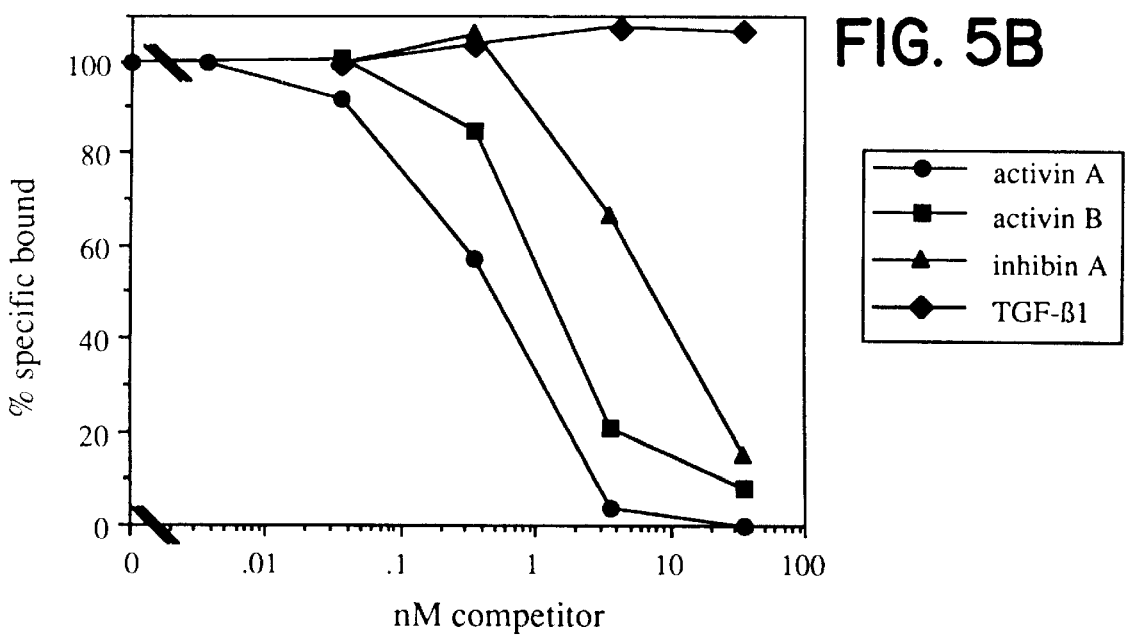
FIG. 5B summarizes results of $^{125}$I activin A binding to COS cells transfected with pmActR2. Binding was competed with unlabeled factors as indicated in the figure. For the runs reported herein, total binding was 3.4% of input cpm, non-specific binding was 0.9% of input cpm, and therefore the specific binding was 2.5% of input cpm. Data are shown as % specific binding, normalized to 100%.

Binding of iodinated activin A to COS cells transiently transfected with pmActR2 could be competed by activin B with slightly reduced potency compared to activin A; by inhibin A with approximately 10-fold lower potency; and could not be competed by TGF-β1 (FIG. 5B). This affinity and specificity of binding match those observed following binding of activin A to a number of other activin-responsive cell types. Although activin B appears to bind the transfected receptor with lower affinity than activin A, the activin B preparation used in these experiments may have suffered a reduction in potency, based on a comparison of bioactivity with activin A, since the recombinant synthesis of the activin B employed herein had been carried out some time ago [recombinant synthesis of activin B is described by Mason et al., in Mol. Endocrinol. 3: 1352–1358 (1989)]. It is likely that this cDNA encodes a receptor for multiple forms of activin.

The size of the cloned activin receptor was analyzed by affinity cross-linking $^{125}$I activin A to COS cells transfected with pmActR2 using the bifunctional chemical cross-linker, disuccinimidyl suberate (DSS). A major cross-linked band of 84 kDa was observed in transfected, but not in untransfected cells. Subtracting the molecular weight of activin, this represents a protein of 56 kDa, which corresponds well to the molecular weight predicted from the nucleic acid sequence data. Cross-linking $^{125}$I activin A to AtT20 cells yields a major band of 65 kDa, with minor bands of approximately 78 and 84 kDa. The size of the largest band matches that generated by the cloned receptor. The smaller bands could be either separate proteins, different phosphorylated forms of the same protein, or degradation products of the full length clone; the sequences DKKRR at amino acid 35 and KKKR at amino acid 416 could be potential sites of proteolysis. Alternatively, these bands could come from alternatively spliced products of the same gene.

The 84 and 65 kDa cross-linked bands have also been observed in other activin-responsive cell types [Hino, supra; Centrella et al., Mol. Cell. Biol. 11: 250–258 (1991)], and interpreted to represent the signalling receptor, although complexes of other sizes have also been seen as well. The size of the activin receptor is very similar to a putative TGF-βreceptor, to the limited extent it has been characterized by chemical cross-linking [see Massague et al., Ann. N.Y. Acad. Sci. 593: 59–72 (1990)].

Example X

Expression of Activin Receptor mRNA

The distribution of activin receptor mRNA was analyzed by Northern blot. Two mRNA species, of 6.0 and 3.0 kb, were observed in AtT20 cells as well as a number of mouse tissues, including brain, testis, pancreas, liver and kidney. The total combined size of the inserts from pmActR1 and pmActR2 is 3.1 kb, which corresponds to the size of the smaller transcript. Neither the extent of similarity between the two mRNAs, nor the significance of having two transcripts is clear. The genes for several other hormone receptors have been shown to be alternatively spliced to generate both a cell surface receptor and a soluble binding protein, and it is possible that the activin receptor is processed in a similar manner.

Interestingly, the relative abundance of the two transcripts varies depending on the source. While AtT20 cells have approximately equal levels of both mRNAs, most tissues had much greater levels of the 6.0 kb transcript, with little or no expression of the 3.0 kb transcript. Testis, on the other hand, had a greater amount of the 3.0 kb band. Expression of activin receptor mRNA in brain, liver and testis is in accord with described biological actions of activin in those tissues [Mine et al., Endocrinol. 125: 586–591 (1989); Vale et al., Peptide Growth Factors and Their Receptors, Handbook of Experimental Pharmacology, M. A. Sporn and A. B. Roberts, ed., Springer-Verlag (1990), in press].

Example XI

Identification of a Human Activin Receptor A human testis library (purchased from Clontech; catalog no. HL1010b) was probed with the full length mouse activin receptor gene (see Sequence ID No. 1) under the following conditions:

Hybridization stringency
  20% formamide, 6×SSC at 42° C.;
Wash stringency
  2>SSC, 0.1% SDS at 42° C.;

A sequence which is highly homologous with the mouse activin receptor was identified (Sequence ID No. 1'). Due to the high degree of homology between this receptor and the mouse activin receptor, this receptor is designated as the human form of the activin receptor from the same subclass as the mouse receptor described above.

Example XII

Identification of a Xenopus Activin Receptor

A Xenopus stage 17 embryo cDNA library (prepared as described by Kintner and Melton in Development 99: 311–325 (1987) was probed with the full length mouse activin receptor gene (see Sequence ID No. 1) under the following conditions:

Hybridization stringency
  20% formamide, 6×SSC at 42° C.;
Wash stringency
  2×SSC, 0.1% SDS at 42° C.

A sequence having a substantial degree of homology with respect to the mouse activin receptor was identified (Sequence ID No. 3). The degree of overall amino acid homology (relative to the mouse activin receptor) is only about 69% (with 77% homology in the intracellular domain and 58% homology in the extracellular domain). Due to the moderate degree of homology between this receptor and the mouse activin receptor, this receptor is designated as an activin receptor from a different subclass than the mouse receptor described above.

Example XIII

Functional Assays of ActRs in Xenopus embryos

To determine whether xActRIIB can transmit a signal in response to activin, xActRIIB RNA was synthesized in vitro and injected into Xenopus embryos at two different concentrations. Injected embryos were allowed to develop to stage 9, at which time animal caps were dissected and treated overnight with different concentrations of activin. The xActRIIB cDNA was cloned into rp64T [see Krieg and Melton in Methods in Enzymology, Abelson and Simon, Eds. (Academic Press, New York, 1987), vol. 155, p. 397] and transcribed in vitro to generate a capped, synthetic xActRIIB RNA [see Melton et al., in Nucleic Acids Res. 12: 7035 (1984) and Kintner in Neuron 1: 545 (1988)]. Embryos at the two- to four-cell stage were injected with about 20 nl of RNA at concentrations of 0.02 ng/nl, or 0.1 ng/nl, spread between four quadrants of the animal pole. At stage 9, animal caps were removed from RNA-injected embryos and incubated in 0.5× modified mammalian Ringer's (MMR), 0.1% bovine serum albumin (BSA) with different concentrations of purified, porcine activin A (six caps per incubation). After 20 hours in culture, total RNA was prepared.

The response of the caps to activin was assessed by quantifying muscle-specific actin RNA with a ribonuclease protection assay as per Blackwell and Weintraub, Science 250: 1104 (1990). Embryos injected with 0.4 and 2.0 ng of xActRIIB RNA were approximately 10- and 100-fold more sensitive, respectively, to activin than control embryos. The low amount of muscle actin found in animal caps in the absence of added activin A is probably a consequence of contamination of the animal cap with a small amount of marginal zone tissue.

The amount of muscle actin decreased with increasing concentration of activin in the embryos injected with 2 ng of xActRIIB RNA. This is consistent with the observation that isolated animal cap cells uniformly exposed to different concentrations of activin only form muscle cells in response to a narrow range of activin concentrations [see Blackmann and Kadesch in Genes and Development 5: 1057 (1990)]. The present results indicate that the concentration of ligand and the amount of receptor are both important in determining the signal transmitted. Thus, the range of activin concentrations that lead to muscle differentiation is lower in animal cap cells from injected embryos, which are expressing more receptor than normal, than from uninjected embryos.

Example XIV

Analysis of kinase activity of mActRII

A fragment of cDNA corresponding to the entire intracellular domain of mActRII (amino acids 143–494) was subcloned into the vector pGEX-2T [see Smith and Johnson in Gene 67: 31–40 (1988)], creating a fusion protein between glutathione S-transferase (GST) and the putative kinase domain of the receptor. This plasmid was introduced into bacteria and the expressed fusion protein was purified using glutathione affinity chromatography as described by Smith and Johnson. Approximately 100–200 ng of fusion protein, or of purified GST, were incubated with 25 $\mu$Ci [$\gamma$-$^{32}$p] ATP in a buffer containing 50 mM Tris, 10 mM MgCl$_2$ for 30 minutes at 37° C. The products were analyzed by SDS-PAGE and autoradiography. The fusion protein, but not the GST alone, became phosphorylated, indicating that the kinase domain of the fusion protein was functional. Phosphoamino acid analysis, performed according to Cooper et al. [Meth. Enzym. 99: 387 (1983)], indicated that the predominant amino acid residue that became phosphorylated was threonine.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence (and the deduced amino acid sequence) of a cDNA encoding a mouse-derived activin receptor of the present invention.

Sequence ID No. 1' is a nucleic acid sequence encoding a human-derived activin receptor of the present invention. Sequence ID No. 1' is substantially the same as Sequence ID No. 1, except that the codon for amino acid residue number 39 encodes lysine (i.e., nucleotides 185–187 are AAA or AAG), the codon for amino acid residue 92 encodes valine (i.e., nucleotides 344–346 are GTN, wherein N is A, C, G or T), and the codon for amino acid residue number 288 encodes glutamine (i.e., nucleotides 932–934 are CAA or CAG).

Sequence ID No. 2 is the deduced amino acid sequence of a mouse-derived activin receptor of the present invention.

Sequence ID No. 2' is an amino acid sequence for a human-derived activin receptor of the present invention. Sequence ID No. 2' is substantially the same as Sequence ID No. 2, except that amino acid residue number 39 is lysine, amino acid residue 92 is valine, and amino acid residue number 288 is glutamine.

Sequence ID No. 3 is the nucleic acid sequence (and the deduced amino acid sequence) of a cDNA encoding a Xenopus-derived activin receptor of the present invention.

Sequence ID No. 4 is the deduced amino acid sequence of a Xenopus-derived activin receptor of the present invention.

Sequence ID No. 5 is the amino acid sequence of the VIB subdomain of the serine kinase consensus sequence.

Sequence ID No. 6 is the amino acid sequence of the VIII subdomain of the serine kinase consensus sequence.

Sequence ID No. 7 is the amino acid sequence of the VIB subdomain of the invention activin receptor.

Sequence ID No. 8 is the amino acid sequence of the VIII subdomain of the invention activin receptor.

Sequence ID No. 9 is the amino acid sequence of the VIB subdomain of the tyrosine kinase consensus sequence.

Sequence ID No. 10 is the amino acid sequence of the VIII subdomain of the tyrosine kinase consensus sequence.

That which is claimed is:

1. An isolated nucleic acid molecule encoding the precursor of a vertebrate activin receptor, the nucleic acid molecule comprising a nucleotide sequence which is:
   (a) the nucleotide sequence of a cDNA molecule present in a vertebrate library, wherein the noncoding strand of the cDNA molecule hybridizes under conditions of low stringency with a probe having a sequence selected from the group consisting of:
      (i) nucleotides 71–1609 of SEQ ID NO: 1;
      (ii) nucleotides 71–1609 of SEQ ID NO: 1, wherein nucleotides 185–187 are replaced by a codon for lysine, nucleotides 344–346 are replaced by a codon for valine, and nucleotides 932–934 are replaced by a codon for glutamine; and
      (iii) nucleotides 468–1997 of SEQ ID NO: 3; or
   (b) a sequence degenerate with the sequence of a cDNA molecule according to (a);
   wherein the precursor comprises an N-terminal signal sequence and the sequence of the mature receptor, the mature receptor having an extracellular ligand-binding domain, a transmembrane domain, and an intracellular serine/threonine kinase domains and wherein activin specifically binds to the mature receptor.

2. An isolated nucleic acid molecule comprising the nucleotide sequence of the contiguous portion of the nucleic acid molecule of claim 1 which encodes a mature vertebrate activin receptor.

3. An isolated nucleic acid molecule according to claim 2, having at least about 70% sequence identity with respect to the contiguous nucleotide sequence of:
   nucleotides 128–1609 of SEQ ID NO:1;
   nucleotides 128–1609 of SEQ ID NO:1, wherein nucleotides 184–187 are replaced by a codon for lysine, nucleotides 344–346 are replaced by a codon for valine, and nucleotides 932–934 are replaced by a codon for glutamine; or
   nucleotides 528–1997 of SEQ ID NO:3.

4. An isolated nucleic acid molecule according to claim 2, having at least about 80% sequence identity with respect to the contiguous nucleotide sequence of:
   nucleotides 128–1609 of SEQ ID NO:1;
   nucleotides 128–1609 of SEQ ID NO:1, wherein nucleotides 185–187 are replaced by a codon for lysine, nucleotides 344–346 are replaced by a codon for valine, and nucleotides 932–934 are replaced by a codon for glutamine; or
   nucleotides 528–1997 of SEQ ID NO:3.

5. An isolated nucleic acid molecule according to claim 2, having at least about 90% sequence identity with respect to the contiguous nucleotide sequence of:
   nucleotides 128–1609 of SEQ ID NO:1;
   nucleotides 128–1609 of SEQ ID NO:1, wherein nucleotides 185–187 are replaced by a codon for lysine, nucleotides 344–346 are replaced by a codon for valine, and nucleotides 932–934 are replaced by a codon for glutamine; or
   nucleotides 528–1997 of SEQ ID NO:3.

6. An isolated nucleic acid molecule comprising the nucleotide sequence of the contiguous portion of the nucleic acid molecule of claim 1 which encodes the extracellular domain of a mature vertebrate activin receptor.

7. An isolated nucleic acid molecule according to claim 6, having at least about 70% sequence identity with respect to the contiguous nucleotide sequence of:
   nucleotides 128–472 of SEQ ID NO:1;
   nucleotides 128–472 of SEQ ID NO:1; wherein nucleotides 185–187 are replaced by a codon for lysine, nucleotides 344–346 are replaced by a codon for valine; or
   nucleotides 528–863 of SEQ ID NO:3.

8. An isolated nucleic acid nucleic acid molecule according to claim 6, having at least about 80% sequence identity with respect to the contiguous nucleotide sequence of:
   nucleotides 128–472 of SEQ ID No:1;
   nucleotides 128–472 of SEQ ID NO:1; wherein nucleotides 185–187 are replaced by a codon for lysine, nucleotides 344–346 are replaced by a codon for valine; or
   nucleotides 528–863 of SEQ ID NO:3.

9. An isolated nucleic acid molecule according to claim 6, having at least about 90% sequence identity with respect to the contiguous nucleotide sequence of:
   nucleotides 128–472 of SEQ ID NO:1;
   nucleotides 128–472 of SEQ ID NO:1; wherein nucleotides 185–187 are replaced by a codon for lysine, nucleotides 344–346 are replaced by a codon for valine; or
   nucleotides 528–863 of SEQ ID NO:3.

10. A vector comprising a nucleic acid molecule according to claim 1.

11. A host cell comprising heterologous nucleic acid having the sequence of a nucleic acid molecule according to claim 1.

12. A host cell comprising a vector according to claim 10.

13. A method for producing an activin-binding protein comprising the step of culturing a host cell according to claim 11 under conditions suitable for expression of the activin receptor-encoding nucleic acid in the cell.

14. A method for producing an activin-binding protein comprising the step of culturing a host cell according to claim 12 under conditions suitable for expression of the activin receptor-encoding nucleic acid in the vector.

15. A vector comprising a nucleic acid molecule according to claim 2.

16. A host cell comprising heterologous nucleic acid having the sequence of a nucleic acid molecule according to claim 2.

17. A host cell comprising a vector according to claim 15.

18. A method for producing an activin-binding protein, comprising, the step of culturing a host cell according to claim 16 under conditions suitable for expression of the activin receptor-encoding nucleic acid in the cell.

19. A method for producing an activin-binding protein, comprising the step of culturing a host cell according to claim 17 under conditions suitable for expression of the activin receptor-encoding nucleic acid in the vector.

20. A vector comprising a nucleic acid molecule according to claim 6.

21. A host cell comprising heterologous nucleic acid having the sequence of a nucleic acid molecule according to claim 6.

22. A host cell comprising a vector according to claim 20.

23. A method for producing an activin-binding protein, comprising the step of culturing a host cell according to claim 21 under conditions suitable for expression of the activin receptor-encoding nucleic acid in the cell.

24. A method for producing an activin-binding protein, comprising the step of culturing a host cell according to claim 22 under conditions suitable for expression of the activin receptor-encoding nucleic acid in the vector.

25. An isolated probe having the nucleotide sequence of a fragment of the coding or noncoding strand of a cDNA molecule according to claim 1, wherein the probe specifically hybridizes to said cDNA in said library under low stringency hybridization conditions.

26. A probe according to claim 25, wherein said probe is labeled with a readily detectable substituent.

27. A probe according to claim 26, wherein said readily detectable substituent is selected from a radiolabeled molecule, a fluorescent molecule, an enzyme, or a specific-binding ligand.

28. A method of identifying a DNA molecule encoding all or part of a receptor of the activin/TGF-superfamily, said method comprising:

contacting a sample comprising vertebrate DNA with a probe according to claim 25; and identifying DNA in the sample that hybridizes to the probe under conditions of at least low stringency; and selecting therefrom a DNA molecule having a nucleotide sequence which corresponds to all or part of a cDNA molecule which is present in a vertebrate library and which encodes a receptor precursor polypeptide comprising an N-terminal signal sequence, an extracellular ligand-binding domain, a transmembrane domain, and an intracellular serine/threonine kinase domain.

29. An isolated nucleic acid molecule encoding the extracellular domain of a mature vertebrate activin receptor, wherein said nucleic acid encodes:

the sequence of amino acids 20–134 set forth in SEQ ID NO: 2;

the sequence of amino acids 20–234 set forth in SEQ ID NO: 2, wherein the arginine residue at position number 39 is replaced by a lysine, and the isoleucine at residue number 92 is replaced by a valine; or the sequence of amino acids 21–132 set forth in SEQ ID NO: 4.

30. An isolated nucleic acid molecule encoding the extracellular domain of a mature vertebrate activin receptor, the nucleic acid molecule comprising a nucleotide sequence having a sequence selected from the group consisting of:

nucleotides 128–472 of SEQ ID NO:1;

nucleotides 128–472 of SEQ ID NO: 1, wherein nucleotides 185–187 are replaced by a codon for lysine, nucleotides 344–346 are replaced by a codon for valine; and nucleotides 528–863 of SEQ ID NO: 3.

31. An isolated nucleic acid molecule encoding a mature vertebrate activin receptor, wherein said nucleic acid encodes:

the sequence of amino acids 20–513 set forth in SEQ ID NO:2;

the sequence of amino acids 20–513 set forth in SEQ ID NO:2, wherein the arginine residue at position number 39 is replaced by a lysine, and the isoleucine at residue number 92 is replaced by a valine; or the sequence of amino acids 21–510 set forth ID SEQ ID NO:4.

32. An isolated nucleic acid molecule encoding a mature vertebrate activin receptor, wherein said nucleic acid encodes:

nucleotides 129–609 of SEQ ID NO:1;

nucleotides 128–1609 of SEQ ID NO:1, wherein nucleotides 185–187 are replaced by a codon for lysine, nucleotides 344–346 are replaced by a codon for valine, and nucleotides 932–934 are replaced by a codon for glutamine; or nucleotides 528–1997 of SEQ ID NO:3.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
      ( A ) LENGTH: 2563 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 71..1609

( x i ) SEQUENCE DESCRIPTION: SEQ ID NO:1:

```
CTCCGAGGAA  GACCCAGGGA  ACTGGATATC  TAGCGAGAAC  TTCCTACGGC  TTCTCCGGCG              60

CCTCGGGAAA  ATG  GGA  GCT  GCT  GCA  AAG  TTG  GCG  TTC  GCC  GTC  TTT  CTT        109
            Met  Gly  Ala  Ala  Ala  Lys  Leu  Ala  Phe  Ala  Val  Phe  Leu
            1                  5                             10

ATC  TCT  TGC  TCT  TCA  GGT  GCT  ATA  CTT  GGC  AGA  TCA  GAA  ACT  CAG  GAG    157
Ile  Ser  Cys  Ser  Ser  Gly  Ala  Ile  Leu  Gly  Arg  Ser  Glu  Thr  Gln  Glu
          15                       20                       25

TGT  CTT  TTC  TTT  AAT  GCT  AAT  TGG  GAA  AGA  GAC  AGA  ACC  AAC  CAG  ACT    205
Cys  Leu  Phe  Phe  Asn  Ala  Asn  Trp  Glu  Arg  Asp  Arg  Thr  Asn  Gln  Thr
30                       35                       40                       45

GGT  GTT  GAA  CCT  TGC  TAT  GGT  GAT  AAA  GAT  AAA  CGG  CGA  CAT  TGT  TTT    253
Gly  Val  Glu  Pro  Cys  Tyr  Gly  Asp  Lys  Asp  Lys  Arg  Arg  His  Cys  Phe
                    50                       55                       60

GCT  ACC  TGG  AAG  AAT  ATT  TCT  GGT  TCC  ATT  GAA  ATA  GTG  AAG  CAA  GGT    301
Ala  Thr  Trp  Lys  Asn  Ile  Ser  Gly  Ser  Ile  Glu  Ile  Val  Lys  Gln  Gly
               65                       70                       75

TGT  TGG  CTG  GAT  GAT  ATC  AAC  TGC  TAT  GAC  AGG  ACT  GAT  TGT  ATA  GAA    349
Cys  Trp  Leu  Asp  Asp  Ile  Asn  Cys  Tyr  Asp  Arg  Thr  Asp  Cys  Ile  Glu
          80                       85                       90

AAA  AAA  GAC  AGC  CCT  GAA  GTG  TAC  TTT  TGT  TGC  TGT  GAG  GGC  AAT  ATG    397
Lys  Lys  Asp  Ser  Pro  Glu  Val  Tyr  Phe  Cys  Cys  Cys  Glu  Gly  Asn  Met
     95                      100                      105

TGT  AAT  GAA  AAG  TTC  TCT  TAT  TTT  CCG  GAG  ATG  GAA  GTC  ACA  CAG  CCC    445
Cys  Asn  Glu  Lys  Phe  Ser  Tyr  Phe  Pro  Glu  Met  Glu  Val  Thr  Gln  Pro
110                     115                      120                      125

ACT  TCA  AAT  CCT  GTT  ACA  CCG  AAG  CCA  CCC  TAT  TAC  AAC  ATT  CTG  CTG    493
Thr  Ser  Asn  Pro  Val  Thr  Pro  Lys  Pro  Pro  Tyr  Tyr  Asn  Ile  Leu  Leu
                    130                      135                      140

TAT  TCC  TTG  GTA  CCA  CTA  ATG  TTA  ATT  GCA  GGA  ATT  GTC  ATT  TGT  GCA    541
Tyr  Ser  Leu  Val  Pro  Leu  Met  Leu  Ile  Ala  Gly  Ile  Val  Ile  Cys  Ala
               145                      150                      155

TTT  TGG  GTG  TAC  AGA  CAT  CAC  AAG  ATG  GCC  TAC  CCT  CCT  GTA  CTT  GTT    589
Phe  Trp  Val  Tyr  Arg  His  His  Lys  Met  Ala  Tyr  Pro  Pro  Val  Leu  Val
          160                      165                      170

CCT  ACT  CAA  GAC  CCA  GGA  CCA  CCC  CCA  CCT  TCC  CCA  TTA  CTA  GGG  TTG    637
Pro  Thr  Gln  Asp  Pro  Gly  Pro  Pro  Pro  Pro  Ser  Pro  Leu  Leu  Gly  Leu
     175                      180                      185

AAG  CCA  TTG  CAG  CTG  TTA  GAA  GTG  AAA  GCA  AGG  GGA  AGA  TTT  GGT  TGT    685
Lys  Pro  Leu  Gln  Leu  Leu  Glu  Val  Lys  Ala  Arg  Gly  Arg  Phe  Gly  Cys
190                      195                      200                      205

GTC  TGG  AAA  GCC  CAG  TTG  CTC  AAT  GAA  TAT  GTG  GCT  GTC  AAA  ATA  TTT    733
Val  Trp  Lys  Ala  Gln  Leu  Leu  Asn  Glu  Tyr  Val  Ala  Val  Lys  Ile  Phe
```

-continued

```
                    210                              215                              220
CCA ATA CAG GAC AAA CAG TCC TGG CAG AAT GAA TAT GAA GTC TAT AGT                          781
Pro Ile Gln Asp Lys Gln Ser Trp Gln Asn Glu Tyr Glu Val Tyr Ser
            225                 230                         235

CTA CCT GGA ATG AAG CAT GAG AAC ATA CTA CAG TTC ATT GGT GCA GAG                          829
Leu Pro Gly Met Lys His Glu Asn Ile Leu Gln Phe Ile Gly Ala Glu
        240                     245                     250

AAA AGA GGC ACC AGT GTG GAT GTG GAC CTG TGG CTA ATC ACA GCA TTT                          877
Lys Arg Gly Thr Ser Val Asp Val Asp Leu Trp Leu Ile Thr Ala Phe
    255                     260                     265

CAT GAA AAG GGC TCA CTG TCA GAC TTT CTT AAG GCT AAT GTG GTC TCT                          925
His Glu Lys Gly Ser Leu Ser Asp Phe Leu Lys Ala Asn Val Val Ser
270                     275                     280                 285

TGG AAT GAA CTT TGT CAT ATT GCA GAA ACC ATG GCT AGA GGA TTG GCA                          973
Trp Asn Glu Leu Cys His Ile Ala Glu Thr Met Ala Arg Gly Leu Ala
                    290                     295                 300

TAT TTA CAT GAG GAT ATA CCT GGC TTA AAA GAT GGC CAC AAG CCT GCA                         1021
Tyr Leu His Glu Asp Ile Pro Gly Leu Lys Asp Gly His Lys Pro Ala
                305                     310                 315

ATC TCT CAC AGG GAC ATC AAA AGT AAA AAT GTG CTG TTG AAA AAC AAT                         1069
Ile Ser His Arg Asp Ile Lys Ser Lys Asn Val Leu Leu Lys Asn Asn
            320                     325                 330

CTG ACA GCT TGC ATT GCT GAC TTT GGG TTG GCC TTA AAG TTC GAG GCT                         1117
Leu Thr Ala Cys Ile Ala Asp Phe Gly Leu Ala Leu Lys Phe Glu Ala
        335                     340                 345

GGC AAG TCT GCA GGT GAC ACC CAT GGG CAG GTT GGT ACC CGG AGG TAT                         1165
Gly Lys Ser Ala Gly Asp Thr His Gly Gln Val Gly Thr Arg Arg Tyr
350                     355                 360                     365

ATG GCT CCA GAG GTG TTG GAG GGT GCT ATA AAC TTC CAA AGG GAC GCA                         1213
Met Ala Pro Glu Val Leu Glu Gly Ala Ile Asn Phe Gln Arg Asp Ala
                    370                 375                     380

TTT CTG AGG ATA GAT ATG TAC GCC ATG GGA TTA GTC CTA TGG GAA TTG                         1261
Phe Leu Arg Ile Asp Met Tyr Ala Met Gly Leu Val Leu Trp Glu Leu
                385                 390                     395

GCT TCT CGT TGC ACT GCT GCA GAT GGA CCC GTA GAT GAG TAC ATG TTA                         1309
Ala Ser Arg Cys Thr Ala Ala Asp Gly Pro Val Asp Glu Tyr Met Leu
            400                 405                     410

CCA TTT GAG GAA GAA ATT GGC CAG CAT CCA TCT CTT GAA GAT ATG CAG                         1357
Pro Phe Glu Glu Glu Ile Gly Gln His Pro Ser Leu Glu Asp Met Gln
        415                 420                     425

GAA GTT GTT GTG CAT AAA AAA AAG AGG CCT GTT TTA AGA GAT TAT TGG                         1405
Glu Val Val Val His Lys Lys Lys Arg Pro Val Leu Arg Asp Tyr Trp
    430                 435                     440                     445

CAG AAA CAT GCA GGA ATG GCA ATG CTC TGT GAA ACG ATA GAA GAA TGT                         1453
Gln Lys His Ala Gly Met Ala Met Leu Cys Glu Thr Ile Glu Glu Cys
                450                     455                     460

TGG GAT CAT GAT GCA GAA GCC AGG TTA TCA GCT GGA TGT GTA GGT GAA                         1501
Trp Asp His Asp Ala Glu Ala Arg Leu Ser Ala Gly Cys Val Gly Glu
                    465                     470                 475

AGA ATT ACT CAG ATG CAA AGA CTA ACA AAT ATC ATT ACT ACA GAG GAC                         1549
Arg Ile Thr Gln Met Gln Arg Leu Thr Asn Ile Ile Thr Thr Glu Asp
                480                     485                 490

ATT GTA ACA GTG GTC ACA ATG GTG ACA AAT GTT GAC TTT CCT CCC AAA                         1597
Ile Val Thr Val Val Thr Met Val Thr Asn Val Asp Phe Pro Pro Lys
            495                     500                 505

GAA TCT AGT CTA TGATGGTGGC ACCGTCTGTA CACACTGAGG ACTGGGACTC                             1649
Glu Ser Ser Leu
510

TGAACTGGAG CTGCTAAGCT AAGGAAAGTG CTTAGTTGAT TTTCTGTGTG AAATGAGTAG                       1709
```

```
GATGCCTCCA  GGACATGTAC  GCAAGCAGCC  CCTTGTGGAA  AGCATGGATC  TGGGAGATGG    1769

ATCTGGGAAA  CTTACTGCAT  CGTCTGCAGC  ACAGATATGA  AGAGGAGTCT  AAGGGAAAAG    1829

CTGCAAACTG  TAAAGAACTT  CTGAAAATGT  ACTCGAAGAA  TGTGGCCCTC  TCCAAATCAA    1889

GGATCTTTTG  GACCTGGCTA  ATCAAGTATT  TGCAAAACTG  ACATCAGATT  TCTTAATGTC    1949

TGTCAGAAGA  CACTAATTCC  TTAAATGAAC  TACTGCTATT  TTTTTAAAT   GAAAAACTTT    2009

TCATTTCAGA  TTTTAAAAAG  GGTAACTTTT  TATTGCATTT  GCTGTTGTTT  CTATAAATGA    2069

CTATTGTAAT  GCCAACATGA  CACAGCTTGT  GAATGTGTAG  TGTGCTGCTG  TTCTGTGTAC    2129

ATAGTCATCA  AAGTGGGGTA  CAGTAAAGAG  GCTTCCAAGC  ATTACTTTAA  CCTCCCTCAA    2189

CAAGGTATAC  CTCAGTTCCA  CGGTTGTTAA  ATTATAAAT   TGAAAACACT  AACAGAATTT    2249

GAATAAATCA  GTCCATGTTT  TATAACAAGG  TTAATTACAA  ATTCACTGTG  TTATTTAAGA    2309

AAAAATGGTA  AGCTATGCTT  AGTGCCAATA  GTAAGTGGCT  ATTTGTAAAG  CAGTGTTTTA    2369

GCTTTTCTTC  TACTGGCTTG  TAATTTAGGG  AAAACAAGTG  CTGTCTTTGA  AATGGAAAAG    2429

AATATGGTGT  CACCCTACCC  CCCATACTTA  TATCAAGGTC  CCAAAATATT  CTTTTCCATT    2489

TCAAAGACAG  CACTTTGAAA  ACCCTAAATT  ACAAGCCAGT  AGAAGAAAAG  CTAAAACACG    2549

CTTTACAAAT  AGCC                                                          2563
```

( 2 ) INFORMATION FOR SEQ ID NO:2:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gly  Ala  Ala  Ala  Lys  Leu  Ala  Phe  Ala  Val  Phe  Leu  Ile  Ser  Cys
 1              5                        10                       15

Ser  Ser  Gly  Ala  Ile  Leu  Gly  Arg  Ser  Glu  Thr  Gln  Glu  Cys  Leu  Phe
                20                        25                       30

Phe  Asn  Ala  Asn  Trp  Glu  Arg  Asp  Arg  Thr  Asn  Gln  Thr  Gly  Val  Glu
           35                        40                       45

Pro  Cys  Tyr  Gly  Asp  Lys  Asp  Lys  Arg  Arg  His  Cys  Phe  Ala  Thr  Trp
     50                        55                       60

Lys  Asn  Ile  Ser  Gly  Ser  Ile  Glu  Ile  Val  Lys  Gln  Gly  Cys  Trp  Leu
 65                       70                       75                       80

Asp  Asp  Ile  Asn  Cys  Tyr  Asp  Arg  Thr  Asp  Cys  Ile  Glu  Lys  Lys  Asp
                85                       90                       95

Ser  Pro  Glu  Val  Tyr  Phe  Cys  Cys  Cys  Glu  Gly  Asn  Met  Cys  Asn  Glu
               100                      105                      110

Lys  Phe  Ser  Tyr  Phe  Pro  Glu  Met  Glu  Val  Thr  Gln  Pro  Thr  Ser  Asn
          115                      120                      125

Pro  Val  Thr  Pro  Lys  Pro  Pro  Tyr  Tyr  Asn  Ile  Leu  Leu  Tyr  Ser  Leu
     130                      135                      140

Val  Pro  Leu  Met  Leu  Ile  Ala  Gly  Ile  Val  Ile  Cys  Ala  Phe  Trp  Val
145                      150                      155                      160

Tyr  Arg  His  His  Lys  Met  Ala  Tyr  Pro  Pro  Val  Leu  Val  Pro  Thr  Gln
                165                      170                      175

Asp  Pro  Gly  Pro  Pro  Pro  Ser  Pro  Leu  Leu  Gly  Leu  Lys  Pro  Leu
               180                      185                      190

Gln  Leu  Leu  Glu  Val  Lys  Ala  Arg  Gly  Arg  Phe  Gly  Cys  Val  Trp  Lys
          195                      200                      205
```

```
Ala  Gln  Leu  Leu  Asn  Glu  Tyr  Val  Ala  Val  Lys  Ile  Phe  Pro  Ile  Gln
     210                      215                 220

Asp  Lys  Gln  Ser  Trp  Gln  Asn  Glu  Tyr  Glu  Val  Tyr  Ser  Leu  Pro  Gly
225                      230                 235                           240

Met  Lys  His  Glu  Asn  Ile  Leu  Gln  Phe  Ile  Gly  Ala  Glu  Lys  Arg  Gly
               245                      250                           255

Thr  Ser  Val  Asp  Val  Asp  Leu  Trp  Leu  Ile  Thr  Ala  Phe  His  Glu  Lys
               260                 265                      270

Gly  Ser  Leu  Ser  Asp  Phe  Leu  Lys  Ala  Asn  Val  Val  Ser  Trp  Asn  Glu
          275                      280                      285

Leu  Cys  His  Ile  Ala  Glu  Thr  Met  Ala  Arg  Gly  Leu  Ala  Tyr  Leu  His
     290                      295                      300

Glu  Asp  Ile  Pro  Gly  Leu  Lys  Asp  Gly  His  Lys  Pro  Ala  Ile  Ser  His
305                      310                 315                           320

Arg  Asp  Ile  Lys  Ser  Lys  Asn  Val  Leu  Leu  Lys  Asn  Asn  Leu  Thr  Ala
               325                      330                      335

Cys  Ile  Ala  Asp  Phe  Gly  Leu  Ala  Leu  Lys  Phe  Glu  Ala  Gly  Lys  Ser
               340                 345                      350

Ala  Gly  Asp  Thr  His  Gly  Gln  Val  Gly  Thr  Arg  Arg  Tyr  Met  Ala  Pro
          355                      360                      365

Glu  Val  Leu  Glu  Gly  Ala  Ile  Asn  Phe  Gln  Arg  Asp  Ala  Phe  Leu  Arg
     370                      375                      380

Ile  Asp  Met  Tyr  Ala  Met  Gly  Leu  Val  Leu  Trp  Glu  Leu  Ala  Ser  Arg
385                      390                 395                           400

Cys  Thr  Ala  Ala  Asp  Gly  Pro  Val  Asp  Glu  Tyr  Met  Leu  Pro  Phe  Glu
               405                 410                      415

Glu  Glu  Ile  Gly  Gln  His  Pro  Ser  Leu  Glu  Asp  Met  Gln  Glu  Val  Val
               420                 425                      430

Val  His  Lys  Lys  Lys  Arg  Pro  Val  Leu  Arg  Asp  Tyr  Trp  Gln  Lys  His
          435                      440                      445

Ala  Gly  Met  Ala  Met  Leu  Cys  Glu  Thr  Ile  Glu  Glu  Cys  Trp  Asp  His
     450                      455                      460

Asp  Ala  Glu  Ala  Arg  Leu  Ser  Ala  Gly  Cys  Val  Gly  Glu  Arg  Ile  Thr
465                      470                 475                           480

Gln  Met  Gln  Arg  Leu  Thr  Asn  Ile  Ile  Thr  Thr  Glu  Asp  Ile  Val  Thr
               485                      490                      495

Val  Val  Thr  Met  Val  Thr  Asn  Val  Asp  Phe  Pro  Pro  Lys  Glu  Ser  Ser
               500                      505                      510

Leu
```

( 2 ) INFORMATION FOR SEQ ID NO:3:

( i ) SEQUENCE CHARACTERISTICS:
        ( A ) LENGTH: 2335 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XACTR ( i x ) FEATURE:
        ( A ) NAME/KEY: CDS
        ( B ) LOCATION: 468..1997

( x i ) SEQUENCE DESCRIPTION: SEQ ID NO:3:

-continued

| | | | | | |
|---|---|---|---|---|---|
| CCGCCCACAC | AGTGCAGTGA | ATAATAGCCG | GTGCGGCCCC | TCCCCTCTTT | CCCTGGCAGT | 60 |
| TGTGTATCTG | TCACATTGAA | GTTTGGGCTC | CTGTGAGTCT | GAGCCTCCCC | CTGTGTCTCA | 120 |
| TGTGAAGCTG | CTGCTGCAGA | AGGTGGAGTC | GTTGCATGAG | GGTGGGGGGA | GTCGCTGCTG | 180 |
| TTTGATCTGC | CTCTGCTCCC | CATTCACACT | CTCATTTCAT | TCCCACGGAT | CCACATTACA | 240 |
| ACTCGCCTTT | AACCCTTTCC | CTGGCGGAGC | CACGCGTCT | TTCATCCCTC | CTGCCGCGGC | 300 |
| CGCTGAGCGA | CCAGAGCGCG | ACATTGTTGC | GGCGGGGGAT | TGGGCGACAT | TGTTGCGAAT | 360 |
| AATCGGAGCT | GCTGGGGGGG | AACTGATACA | ACGTTGCGAC | TGTAAAGGAA | TTAACTCGGC | 420 |
| CGAATGGGAT | TTTATCTGTG | TCGGTGAGAG | AAGCGGATCC | CAGGAGC ATG GGG GCG | | 476 |
| | | | | Met Gly Ala | |
| | | | | 1 | |

```
TCT GTA GCG CTG ACT TTT CTA CTT CTT CTT GCA ACT TTC CGC GCA GGC        524
Ser Val Ala Leu Thr Phe Leu Leu Leu Leu Ala Thr Phe Arg Ala Gly
         5                  10                  15

TCA GGA CAC GAT GAA GTG GAG ACA AGA GAG TGC ATC TAT TAC AAT GCC        572
Ser Gly His Asp Glu Val Glu Thr Arg Glu Cys Ile Tyr Tyr Asn Ala
 20                  25                  30                  35

AAC TGG GAA CTG GAG AAG ACC AAC CAA AGT GGG GTG GAA AGC TGC GAA        620
Asn Trp Glu Leu Glu Lys Thr Asn Gln Ser Gly Val Glu Ser Cys Glu
                 40                  45                  50

GGG GAA AAG GAC AAG CGA CTC CAC TGT TAC GCG TCT TGG AGG AAC AAT        668
Gly Glu Lys Asp Lys Arg Leu His Cys Tyr Ala Ser Trp Arg Asn Asn
             55                  60                  65

TCG GGC TTC ATA GAG CTG GTG AAA AAA GGA TGC TGG CTG GAT GAC TTC        716
Ser Gly Phe Ile Glu Leu Val Lys Lys Gly Cys Trp Leu Asp Asp Phe
         70                  75                  80

AAC TGT TAT GAC AGA CAG GAA TGT ATT GCC AAG GAA GAA AAC CCC CAA        764
Asn Cys Tyr Asp Arg Gln Glu Cys Ile Ala Lys Glu Glu Asn Pro Gln
 85                  90                  95

GTC TTT TTC TGC TGC TGC GAG GGA AAC TAC TGC AAC AAG AAA TTT ACT        812
Val Phe Phe Cys Cys Cys Glu Gly Asn Tyr Cys Asn Lys Lys Phe Thr
100                 105                 110                 115

CAT TTG CCT GAA GTC GAA ACA TTT GAT CCG AAG CCC CAG CCG TCA GCC        860
His Leu Pro Glu Val Glu Thr Phe Asp Pro Lys Pro Gln Pro Ser Ala
                120                 125                 130

TCC GTA CTG AAC ATT CTG ATC TAT TCC CTG CTT CCA ATT GTT GGT CTT        908
Ser Val Leu Asn Ile Leu Ile Tyr Ser Leu Leu Pro Ile Val Gly Leu
            135                 140                 145

TCC ATG GCA ATT CTC CTG GCG TTC TGG ATG TAC CGT CAT CGA AAG CCT        956
Ser Met Ala Ile Leu Leu Ala Phe Trp Met Tyr Arg His Arg Lys Pro
        150                 155                 160

CCC TAC GGG CAT GTA GAG ATC AAT GAG GAC CCC GGT CTG CCC CCT CCA       1004
Pro Tyr Gly His Val Glu Ile Asn Glu Asp Pro Gly Leu Pro Pro Pro
165                 170                 175

TCT CCT CTG GTC GGG CTG AAG CCG CTG CAG TTG CTG GAG ATA AAG GCG       1052
Ser Pro Leu Val Gly Leu Lys Pro Leu Gln Leu Leu Glu Ile Lys Ala
180                 185                 190                 195

CGA GGC CGT TTC GGT TGC GTC TGG AAA GCT CGT CTG CTG AAT GAA TAT       1100
Arg Gly Arg Phe Gly Cys Val Trp Lys Ala Arg Leu Leu Asn Glu Tyr
                200                 205                 210

GTC GCA GTG AAA ATC TTC CCC GTG CAG GAT AAG CAG TCG TGG CAG TGT       1148
Val Ala Val Lys Ile Phe Pro Val Gln Asp Lys Gln Ser Trp Gln Cys
            215                 220                 225

GAG AAA GAG ATC TTC ACC ACG CCG GGC ATG AAA CAT GAA AAC CTA TTG       1196
Glu Lys Glu Ile Phe Thr Thr Pro Gly Met Lys His Glu Asn Leu Leu
        230                 235                 240

GAG TTC ATT GCC GCT GAG AAG AGG GGA AGC AAC CTG GAG ATG GAG CTG       1244
Glu Phe Ile Ala Ala Glu Lys Arg Gly Ser Asn Leu Glu Met Glu Leu
```

```
                 245                            250                            255
TGG  CTC  ATC  ACT  GCA  TTT  CAT  GAT  AAG  GGT  TCT  CTG  ACG  GAC  TAC  CTG         1292
Trp  Leu  Ile  Thr  Ala  Phe  His  Asp  Lys  Gly  Ser  Leu  Thr  Asp  Tyr  Leu
260                      265                      270                      275

AAA  GGG  AAC  TTG  GTG  AGC  TGG  AAT  GAA  CTG  TGT  CAC  ATA  ACA  GAA  ACA         1340
Lys  Gly  Asn  Leu  Val  Ser  Trp  Asn  Glu  Leu  Cys  His  Ile  Thr  Glu  Thr
                    280                      285                      290

ATG  GCT  CGT  GGG  CTG  GCC  TAC  TTA  CAT  GAA  GAT  GTG  CCC  CGC  TGT  AAA         1388
Met  Ala  Arg  Gly  Leu  Ala  Tyr  Leu  His  Glu  Asp  Val  Pro  Arg  Cys  Lys
               295                      300                      305

GGT  GAA  GGG  CAC  AAA  CCT  GCA  ATC  GCT  CAC  AGA  GAT  TTT  AAA  AGT  AAG         1436
Gly  Glu  Gly  His  Lys  Pro  Ala  Ile  Ala  His  Arg  Asp  Phe  Lys  Ser  Lys
          310                      315                      320

AAT  GTA  TTG  CTA  AGA  AAC  GAC  CTG  ACT  GCG  ATA  TTA  GCA  GAC  TTC  GGG         1484
Asn  Val  Leu  Leu  Arg  Asn  Asp  Leu  Thr  Ala  Ile  Leu  Ala  Asp  Phe  Gly
     325                      330                      335

CTG  GCC  GTA  CGA  TTT  GAG  CCT  GGA  AAA  CCT  CCG  GGA  GAT  ACA  CAC  GGG         1532
Leu  Ala  Val  Arg  Phe  Glu  Pro  Gly  Lys  Pro  Pro  Gly  Asp  Thr  His  Gly
340                      345                      350                      355

CAG  GTT  GGC  ACC  AGG  AGG  TAT  ATG  GCT  CCT  GAG  GTT  CTA  GAG  GGA  GCA         1580
Gln  Val  Gly  Thr  Arg  Arg  Tyr  Met  Ala  Pro  Glu  Val  Leu  Glu  Gly  Ala
                    360                      365                      370

ATT  AAC  TTT  CAG  CGA  GAT  TCC  TTT  CTC  AGG  ATA  GAT  ATG  TAT  GCC  ATG         1628
Ile  Asn  Phe  Gln  Arg  Asp  Ser  Phe  Leu  Arg  Ile  Asp  Met  Tyr  Ala  Met
               375                      380                      385

GGA  CTG  GTA  CTC  TGG  GAA  ATA  GTA  TCC  CGA  TGT  ACA  GCA  GCA  GAT  GGG         1676
Gly  Leu  Val  Leu  Trp  Glu  Ile  Val  Ser  Arg  Cys  Thr  Ala  Ala  Asp  Gly
          390                      395                      400

CCA  GTA  GAT  GAG  TAT  CTG  CTC  CCA  TTC  GAA  GAA  GAG  ATT  GGG  CAA  CAT         1724
Pro  Val  Asp  Glu  Tyr  Leu  Leu  Pro  Phe  Glu  Glu  Glu  Ile  Gly  Gln  His
     405                      410                      415

CCT  TCC  CTA  GAG  GAT  CTG  CAA  GAA  GTT  GTC  GTT  CAC  AAG  AAG  ATA  CGC         1772
Pro  Ser  Leu  Glu  Asp  Leu  Gln  Glu  Val  Val  Val  His  Lys  Lys  Ile  Arg
420                      425                      430                      435

CCT  GTA  TTC  AAA  GAC  CAC  TGG  CTG  AAA  CAC  CCT  GGT  CTG  GCC  CAA  CTG         1820
Pro  Val  Phe  Lys  Asp  His  Trp  Leu  Lys  His  Pro  Gly  Leu  Ala  Gln  Leu
                    440                      445                      450

TGC  GTC  ACC  ATT  GAA  GAA  TGC  TGG  GAC  CAT  GAT  GCG  GAA  GCA  CGG  CTT         1868
Cys  Val  Thr  Ile  Glu  Glu  Cys  Trp  Asp  His  Asp  Ala  Glu  Ala  Arg  Leu
               455                      460                      465

TCG  GCA  GGC  TGC  GTA  GAG  GAG  CGT  ATT  TCC  CAA  ATC  CGT  AAA  TCA  GTG         1916
Ser  Ala  Gly  Cys  Val  Glu  Glu  Arg  Ile  Ser  Gln  Ile  Arg  Lys  Ser  Val
          470                      475                      480

AAC  GGC  ACT  ACC  TCG  GAC  TGC  CTT  GTA  TCC  ATT  GTT  ACA  TCT  GTC  ACC         1964
Asn  Gly  Thr  Thr  Ser  Asp  Cys  Leu  Val  Ser  Ile  Val  Thr  Ser  Val  Thr
     485                      490                      495

AAT  GTG  GAC  TTG  CCG  CCC  AAA  GAG  TCC  AGT  ATC  TGAGGTTTCT TTGGTCTTTC            2017
Asn  Val  Asp  Leu  Pro  Pro  Lys  Glu  Ser  Ser  Ile
500                      505                      510

CAGACTCAGT GACTTTTAAA AAAAAAACTC ACGAATGCAG CTGCTATTTT ATCTTGACTT                       2077

TTTAATATTT TTTTCTTGG  ATTTTACTTG GATCGGATCA ATTTACCAGC ACGTCATTCG                       2137

AAAGTATTAA AAAAAAAAAA CAAAACAAAA AAGCAAAAAC AGACATCTCA GCAAGCATTC                       2197

AGGTGCCGAC TTATGAATGC CAATAGGTGC AGGAACTTCA GAACCTCAAC AAACTCATTT                       2257

CTAGAGAATG TTCTCCTGGT TTCCTTTATC TCAGAAGAGG ACCCATAGGA AAACACCTAA                       2317

GTCAAGCAAA TGCTGCAG                                                                     2335
```

( 2 ) INFORMATION FOR SEQ ID NO:4:

( i ) SEQUENCE CHARACTERISTICS:
    ( A ) LENGTH: 510 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met  Gly  Ala  Ser  Val  Ala  Leu  Thr  Phe  Leu  Leu  Leu  Ala  Thr  Phe
 1              5                        10                        15

Arg  Ala  Gly  Ser  Gly  His  Asp  Glu  Val  Glu  Thr  Arg  Glu  Cys  Ile  Tyr
               20                       25                        30

Tyr  Asn  Ala  Asn  Trp  Glu  Leu  Glu  Lys  Thr  Asn  Gln  Ser  Gly  Val  Glu
               35                       40                        45

Ser  Cys  Glu  Gly  Glu  Lys  Asp  Lys  Arg  Leu  His  Cys  Tyr  Ala  Ser  Trp
     50                       55                        60

Arg  Asn  Asn  Ser  Gly  Phe  Ile  Glu  Leu  Val  Lys  Lys  Gly  Cys  Trp  Leu
 65                           70                        75                    80

Asp  Asp  Phe  Asn  Cys  Tyr  Asp  Arg  Gln  Glu  Cys  Ile  Ala  Lys  Glu  Glu
                    85                        90                        95

Asn  Pro  Gln  Val  Phe  Phe  Cys  Cys  Glu  Gly  Asn  Tyr  Cys  Asn  Lys
                    100                      105                      110

Lys  Phe  Thr  His  Leu  Pro  Glu  Val  Glu  Thr  Phe  Asp  Pro  Lys  Pro  Gln
               115                      120                      125

Pro  Ser  Ala  Ser  Val  Leu  Asn  Ile  Leu  Ile  Tyr  Ser  Leu  Leu  Pro  Ile
     130                      135                      140

Val  Gly  Leu  Ser  Met  Ala  Ile  Leu  Leu  Ala  Phe  Trp  Met  Tyr  Arg  His
145                           150                      155                      160

Arg  Lys  Pro  Pro  Tyr  Gly  His  Val  Glu  Ile  Asn  Glu  Asp  Pro  Gly  Leu
                    165                      170                      175

Pro  Pro  Pro  Ser  Pro  Leu  Val  Gly  Leu  Lys  Pro  Leu  Gln  Leu  Leu  Glu
               180                      185                      190

Ile  Lys  Ala  Arg  Gly  Arg  Phe  Gly  Cys  Val  Trp  Lys  Ala  Arg  Leu  Leu
     195                      200                      205

Asn  Glu  Tyr  Val  Ala  Val  Lys  Ile  Phe  Pro  Val  Gln  Asp  Lys  Gln  Ser
     210                      215                      220

Trp  Gln  Cys  Glu  Lys  Glu  Ile  Phe  Thr  Thr  Pro  Gly  Met  Lys  His  Glu
225                           230                      235                      240

Asn  Leu  Leu  Glu  Phe  Ile  Ala  Ala  Glu  Lys  Arg  Gly  Ser  Asn  Leu  Glu
                    245                      250                      255

Met  Glu  Leu  Trp  Leu  Ile  Thr  Ala  Phe  His  Asp  Lys  Gly  Ser  Leu  Thr
               260                      265                      270

Asp  Tyr  Leu  Lys  Gly  Asn  Leu  Val  Ser  Trp  Asn  Glu  Leu  Cys  His  Ile
          275                      280                      285

Thr  Glu  Thr  Met  Ala  Arg  Gly  Leu  Ala  Tyr  Leu  His  Glu  Asp  Val  Pro
     290                      295                      300

Arg  Cys  Lys  Gly  Glu  Gly  His  Lys  Pro  Ala  Ile  Ala  His  Arg  Asp  Phe
305                      310                      315                      320

Lys  Ser  Lys  Asn  Val  Leu  Leu  Arg  Asn  Asp  Leu  Thr  Ala  Ile  Leu  Ala
                    325                      330                      335

Asp  Phe  Gly  Leu  Ala  Val  Arg  Phe  Glu  Pro  Gly  Lys  Pro  Pro  Gly  Asp
               340                      345                      350

Thr  His  Gly  Gln  Val  Gly  Thr  Arg  Arg  Tyr  Met  Ala  Pro  Glu  Val  Leu
     355                      360                      365

Glu  Gly  Ala  Ile  Asn  Phe  Gln  Arg  Asp  Ser  Phe  Leu  Arg  Ile  Asp  Met
```

|           |     |     |     | 370 |     |     |     | 375 |     |     |     | 380 |     |     |
|-----------|-----|-----|-----|-----|-----|-----|-----|-----|-----|-----|-----|-----|-----|-----|
| Tyr 385   | Ala | Met | Gly | Leu | Val 390 | Leu | Trp | Glu | Ile | Val 395 | Ser | Arg | Cys | Thr | Ala 400 |
| Ala | Asp | Gly | Pro | Val 405 | Asp | Glu | Tyr | Leu | Leu 410 | Pro | Phe | Glu | Glu | Ile 415 |
| Gly | Gln | His | Pro 420 | Ser | Leu | Glu | Asp | Leu 425 | Gln | Glu | Val | Val | Val 430 | His | Lys |
| Lys | Ile | Arg 435 | Pro | Val | Phe | Lys | Asp 440 | His | Trp | Leu | Lys | His 445 | Pro | Gly | Leu |
| Ala | Gln 450 | Leu | Cys | Val | Thr | Ile 455 | Glu | Glu | Cys | Trp | Asp 460 | His | Asp | Ala | Glu |
| Ala 465 | Arg | Leu | Ser | Ala | Gly 470 | Cys | Val | Glu | Glu | Arg 475 | Ile | Ser | Gln | Ile | Arg 480 |
| Lys | Ser | Val | Asn | Gly 485 | Thr | Thr | Ser | Asp | Cys 490 | Leu | Val | Ser | Ile | Val 495 | Thr |
| Ser | Val | Thr | Asn 500 | Val | Asp | Leu | Pro | Pro 505 | Lys | Glu | Ser | Ser | Ile 510 |

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: both ( i i ) MOLECULE TYPE: protein ( v ) FRAGMENT TYPE: internal ( x i ) SEQUENCE DESCRIPTION: SEQ ID NO:5:

Asp Leu Lys Pro Glu Asn
1                5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: both ( i i ) MOLECULE TYPE: protein ( v ) FRAGMENT TYPE: internal ( i x ) FEATURE:
        ( A ) NAME/KEY: Modified-site
        ( B ) LOCATION: 2
        ( D ) OTHER INFORMATION: /note= "Xaa at position 2 is either
           "Thr"or "Ser"."

( i x ) FEATURE:
        ( A ) NAME/KEY: Modified-site
        ( B ) LOCATION: 5
        ( D ) OTHER INFORMATION: /note= "Xaa a position 5 is either
           "Tyr"or "Phe"."

( x i ) SEQUENCE DESCRIPTION: SEQ ID NO:6:

Gly Xaa Xaa Xaa Xaa Xaa
1                5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: both -continued (i i) MOLECULE TYPE: protein (v) FRAGMENT TYPE: internal (x i) SEQUENCE DESCRIPTION: SEQ ID NO:7:

Asp Ile Lys Ser Lys Asn
1               5

(2) INFORMATION FOR SEQ ID NO:8:

(i) SEQUENCE CHARACTERISTICS:
    (A) LENGTH: 6 amino acids
    (B) TYPE: amino acid
    (D) TOPOLOGY: both (i i) MOLECULE TYPE: protein (v) FRAGMENT TYPE: internal (x i) SEQUENCE DESCRIPTION: SEQ ID NO:8:

Gly Thr Arg Arg Tyr Met
1               5

(2) INFORMATION FOR SEQ ID NO:9:

(i) SEQUENCE CHARACTERISTICS:
    (A) LENGTH: 6 amino acids
    (B) TYPE: amino acid
    (D) TOPOLOGY: unknown (i i) MOLECULE TYPE: protein (v) FRAGMENT TYPE: internal (x i) SEQUENCE DESCRIPTION: SEQ ID NO:9:

Asp Leu Ala Ala Arg Asn
1               5

(2) INFORMATION FOR SEQ ID NO:10:

(i) SEQUENCE CHARACTERISTICS:
    (A) LENGTH: 6 amino acids
    (B) TYPE: amino acid
    (D) TOPOLOGY: both (i i) MOLECULE TYPE: protein (v) FRAGMENT TYPE: internal (i x) FEATURE:
    (A) NAME/KEY: Modified-site
    (B) LOCATION: 3
    (D) OTHER INFORMATION: /note= "Xaa at position 3 is either
        "Ile"or "Val"."

(i x) FEATURE:
    (A) NAME/KEY: Modified-site
    (B) LOCATION: 4
    (D) OTHER INFORMATION: /note= "Xaa at position 4 is either
        "Lys"or "Arg"."

(i x) FEATURE:
    (A) NAME/KEY: Modified-site
    (B) LOCATION: 6
    (D) OTHER INFORMATION: /note= "Xaa at position 6 is either
        "Thr"or "Met"."

(x i) SEQUENCE DESCRIPTION: SEQ ID NO:10:

Xaa Pro Xaa Xaa Trp Xaa
1               5